United States Patent
Docherty et al.

(10) Patent No.: US 11,311,559 B2
(45) Date of Patent: *Apr. 26, 2022

(54) COMPOSITIONS AND METHODS FOR ENHANCED DELIVERY OF ANTIVIRAL AGENTS

(71) Applicant: POVIVA CORP., Carson City, NV (US)

(72) Inventors: John Docherty, Port Perry (CA); Christopher Andrew Bunka, Kelowna (CA)

(73) Assignee: POVIVA CORP., Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/234,744

(22) Filed: Apr. 19, 2021

(65) Prior Publication Data

US 2022/0054495 A1     Feb. 24, 2022

Related U.S. Application Data

(60) Provisional application No. 63/012,652, filed on Apr. 20, 2020.

(51) Int. Cl.

| | |
|---|---|
| A61K 31/536 | (2006.01) |
| A61K 31/343 | (2006.01) |
| A61K 31/422 | (2006.01) |
| A61K 31/40 | (2006.01) |
| A61K 31/445 | (2006.01) |
| A61K 47/16 | (2006.01) |
| A61K 47/46 | (2006.01) |
| A61K 47/10 | (2017.01) |
| A61K 47/36 | (2006.01) |
| A61K 31/635 | (2006.01) |
| A61K 9/107 | (2006.01) |
| A61K 31/403 | (2006.01) |
| A61K 31/496 | (2006.01) |
| A61K 31/513 | (2006.01) |
| A61K 31/435 | (2006.01) |
| A61K 31/427 | (2006.01) |
| A61K 31/4709 | (2006.01) |
| A61K 31/497 | (2006.01) |
| A61K 31/4433 | (2006.01) |
| A61K 31/4439 | (2006.01) |
| A61K 31/505 | (2006.01) |
| A61K 31/165 | (2006.01) |
| A61K 31/675 | (2006.01) |
| A61K 31/551 | (2006.01) |
| A61K 31/7072 | (2006.01) |
| A61K 47/44 | (2017.01) |
| A61K 31/575 | (2006.01) |
| A61K 35/413 | (2015.01) |
| A61K 31/4418 | (2006.01) |
| A61K 31/506 | (2006.01) |
| A61K 31/7064 | (2006.01) |

(52) U.S. Cl.
CPC ............ *A61K 31/635* (2013.01); *A61K 9/107* (2013.01); *A61K 31/165* (2013.01); *A61K 31/343* (2013.01); *A61K 31/40* (2013.01); *A61K 31/403* (2013.01); *A61K 31/422* (2013.01); *A61K 31/427* (2013.01); *A61K 31/435* (2013.01); *A61K 31/445* (2013.01); *A61K 31/4418* (2013.01); *A61K 31/4433* (2013.01); *A61K 31/4439* (2013.01); *A61K 31/4709* (2013.01); *A61K 31/496* (2013.01); *A61K 31/497* (2013.01); *A61K 31/505* (2013.01); *A61K 31/506* (2013.01); *A61K 31/513* (2013.01); *A61K 31/536* (2013.01); *A61K 31/551* (2013.01); *A61K 31/575* (2013.01); *A61K 31/675* (2013.01); *A61K 31/7064* (2013.01); *A61K 31/7072* (2013.01); *A61K 35/413* (2013.01); *A61K 47/10* (2013.01); *A61K 47/36* (2013.01); *A61K 47/44* (2013.01); *A61K 47/46* (2013.01)

(58) Field of Classification Search
CPC .. A61K 31/535; A61K 31/506; A61K 31/422; A61K 31/40; A61K 31/4439; A61K 31/7054; A61K 31/445; A61K 31/343; A61K 31/165; A61K 31/505; A61K 31/496; A61K 47/46; A61K 47/10; A61K 47/36
USPC .......................................................... 514/49
See application file for complete search history.

(56) References Cited

U.S. PATENT DOCUMENTS

| | | | |
|---|---|---|---|
| 4,830,862 A | 5/1989 | Braun et al. | |
| 5,118,511 A | 6/1992 | Hom et al. | |
| 5,284,674 A | 2/1994 | Fazio | |
| 5,554,400 A | 9/1996 | Stipp | |

(Continued)

FOREIGN PATENT DOCUMENTS

| | | |
|---|---|---|
| CN | 102845568 A1 | 1/2013 |
| DE | 19746830 C1 | 8/1998 |

(Continued)

OTHER PUBLICATIONS

Dixit et al, (Intl. J. Pharm. Sci. Res., 2015, 6(9), 3990-3999.*

(Continued)

*Primary Examiner* — Ganapathy Krishnan
(74) *Attorney, Agent, or Firm* — FisherBroyles LLP; Anthony J Do Vale

(57) ABSTRACT

Disclosed herein are methods, compositions and kits for treating a viral infection, for example, COVID-19, MERS and SARS. The disclosed compositions provide for enhanced delivery of the disclosed antiviral agents.

21 Claims, 2 Drawing Sheets

(56) References Cited

U.S. PATENT DOCUMENTS

| | | |
|---|---|---|
| 5,674,522 A | 10/1997 | Shah |
| 5,895,672 A | 4/1999 | Cooper |
| 5,989,583 A | 11/1999 | Amselem |
| 6,207,203 B1 | 3/2001 | Atkinson |
| 6,365,176 B1 | 4/2002 | Bell |
| 6,887,493 B2 | 5/2005 | Shefer et al. |
| 7,147,882 B2 | 12/2006 | Girsh |
| 7,951,401 B2 | 5/2011 | Colombo |
| 8,435,982 B2 | 5/2013 | Macheras |
| 8,734,885 B2 | 5/2014 | Sweeney |
| 8,808,734 B2 | 8/2014 | Winnicki |
| 8,980,941 B2 | 3/2015 | Hospodor |
| 9,474,725 B1 | 10/2016 | Reillo |
| 9,972,680 B2 | 5/2018 | Reillo |
| 9,974,739 B2 | 5/2018 | Reillo |
| 10,103,225 B2 | 10/2018 | Reillo |
| 10,381,440 B2 | 8/2019 | Reillo |
| 2002/0188024 A1 | 12/2002 | Chilton et al. |
| 2003/0087937 A1 | 5/2003 | Lindberg |
| 2004/0234579 A1 | 11/2004 | Finke |
| 2005/0031761 A1 | 2/2005 | Brucker |
| 2006/0051406 A1* | 3/2006 | Parmar ............... A61K 9/127 424/450 |
| 2007/0213298 A1 | 9/2007 | Rongved et al. |
| 2008/0008781 A1 | 1/2008 | Sweeney et al. |
| 2008/0254153 A1 | 10/2008 | Wang et al. |
| 2008/0299209 A1 | 12/2008 | Beck |
| 2009/0162524 A1 | 6/2009 | Rivera et al. |
| 2009/0264475 A1 | 10/2009 | Schwartz |
| 2010/0267705 A1 | 10/2010 | Macheras |
| 2012/0043242 A1 | 2/2012 | Hospodor |
| 2012/0095087 A1 | 4/2012 | Hyatt |
| 2013/0078356 A1 | 3/2013 | Mackereth et al. |
| 2013/0089600 A1 | 4/2013 | Winnicki |
| 2013/0164412 A1 | 6/2013 | Amrani |
| 2013/0196022 A1 | 8/2013 | Holma |
| 2013/0296415 A1 | 11/2013 | Goskonda et al. |
| 2013/0309291 A1 | 11/2013 | Stoll |
| 2013/0337113 A1 | 12/2013 | Clark et al. |
| 2014/0295049 A1 | 10/2014 | Ragot et al. |
| 2014/0328997 A1 | 11/2014 | Raskin et al. |
| 2014/0370181 A1 | 12/2014 | Young et al. |
| 2015/0057342 A1 | 2/2015 | Koren et al. |
| 2015/0079235 A1 | 3/2015 | Wright et al. |
| 2015/0182455 A1 | 7/2015 | Llamas |
| 2015/0283072 A1 | 10/2015 | Popitz |
| 2015/0352044 A1 | 12/2015 | Benson et al. |
| 2016/0044934 A1 | 2/2016 | Bhairam |
| 2016/0243177 A1 | 8/2016 | Franklin et al. |
| 2016/0324776 A1 | 11/2016 | Glatzel |
| 2016/0324777 A1 | 11/2016 | Victor et al. |
| 2017/0340562 A9 | 11/2017 | Glatzel |
| 2019/0035890 A1 | 1/2019 | Reillo |

FOREIGN PATENT DOCUMENTS

| | | |
|---|---|---|
| JP | S60153779 A | 8/1985 |
| JP | 2001508768 A | 7/2001 |
| JP | 2009508508 A | 3/2009 |
| JP | 2009542224 A | 12/2009 |
| RU | 2030878 C1 | 3/1995 |
| WO | 2007047237 C1 | 3/1995 |
| WO | 9935917 A1 | 7/1999 |
| WO | 2013138906 A1 | 7/1999 |
| WO | 2006063109 | 6/2006 |
| WO | 2007064225 A1 | 6/2007 |
| WO | 2009077188 A1 | 6/2009 |
| WO | 2012106582 | 8/2012 |
| WO | 2012130278 A1 | 10/2012 |
| WO | 2013138906 A1 | 9/2013 |
| WO | 2014076432 A1 | 5/2014 |
| WO | 2014186896 A1 | 11/2014 |
| WO | 2015024055 A1 | 2/2015 |
| WO | 2015191728 A1 | 12/2015 |
| WO | 2016186735 A1 | 11/2016 |
| WO | 2017100062 A1 | 6/2017 |
| WO | 2017100063 A2 | 6/2017 |
| WO | 2018232422 A1 | 12/2018 |

OTHER PUBLICATIONS

Gupta et al, Pharma Science Monitor, 2017, 8(4), 302-306.*
Montenegro et al, in Gum Arabic: More Than an Edible Emulsifier, Products and Applications of Biopolymers, Dr. Johen Verbeek, Ed. 2012, pp. 1-26.*
Chiang, Compr. Physiol. 2013, 3(3), 1191-1212.*
Lipasek et al, Food Research International, 2012, 45, 369-380.*
International Search Report and Written Opinion dated Sep. 11, 2015 for corresponding PCT application No. PCT/US15/35128, and references cited therein.
Kumar, Md, Ashir, et al., Sweeteners, Flavorings, and Dyes in Antibiotic Preparations, Pediatrics, Mar. 3, 1991, pp. 352-360, vol. 87, No. 3, East Lansing, Michigan, US.
Mechoulam, Raphael, et al., Cannabidiol: An Overview of Some Pharmacological Aspects, Journal of Clinical Pharmacology, 2002, vol. 42, pp. 11S-19S.
Jhoo, Jin-Woo, et al., Enzymatic Synthesis of Theaflavins and Epitheaflavic Acid From Tea Catechins and Their Antioxidant Activity, Journal of Food Lipids 11, 2004, pp. 89-103.
Zuardi, Antonio Waldo, Cannabidiol: from an inactive cannabinoid to a drug with wide spectrum of action, Rev Bras Psiquiatr, 2008; 30(3), pp. 271-280.
Fang, Jun, et al., Therapeutic strategies by modulating oxygen stress in cancer and inflammation, Advanced Drug Delivery Reviews 61, 2009, pp. 290-302.
Korte, G., et al., Tea catechiins' affinity for human cannabinoid receptors, Phytomedicine 17, 2010, pp. 19-22.
Lin Daren, et al., Palatability, adherence and prescribing patterns of antiretroviral drugs for children with human immunodeficiency virus infection in Canada, Pharmacoepidemiology and Drug Safety, 2011; 20; pp. 1246-1252.
Booz, George W., Cannabidiol as an emergent therapeutic strategy for lessing the impact of inflammation on oxidative stress, Free Radical Biology & Medicine 51, 2011, pp. 1054-1061.
Alger, Bradley E., et al., Supply and demand for endocannabinoids, Trends in Neurosciences, vol. 34, No. 6, Jun. 2011, pp. 304-315.
Peng, Cheng, et al., Biology of Ageing and Role of Dietary Antioxidants, Hindawi Publishing Corporation, BioMed Research International, vol. 2014, Article ID 831841, pp. 1-13.
Walsh, Jennifer, et al., Playing hide and seek with poorly tasting paediatric medicines: Do not forget the excipients, Advanced Drug Delivery Reviews 73, 2014, pp. 14-33.
McClements, David Julian, et al., Excipient foods: designing food matrices that improve the oral bioavailability of pharmaceuticals and nutraceuticals, Food and Function, The Royal Society of Chemistry, vol. 5, 2014, pp. 1320-1333.
Patrician, A. et al. "Examination of a new Delivery Approach for Oral Cannabindio in Healthy Subjects. A1 Randomized, Double Blinded, Placebo-Controlled Pharmacokinetics Study," Advanced Therapeutics, published on—Sep. 12, 2019.
Chen et al., The relationships of high-fat diet and metabolism of lipophilic vitamins, Integr Food Nutr Metab, 2015, vol. 2(3): 174-179. (Year: 2015).
"Corn Fiber Yields Oil and Gum Products", Agricultural Research, Dec. 1997, pp. 12-13. (Year: 1997).
Indian Patent Application No. 201847025157, Office Action dated May 27, 2020.
EP 16 873 619.7 Examination Report dated Nov. 4, 2019.
EP 16 873 619.7 Response to Examination Report dated Nov. 4, 2019, filed May 1, 2020.
EP Application No. 15806768.6 Extended European Search Report and Written Opinion, dated Nov. 24, 2017.
Leizer et al., The Composition of Hemp Seed Oil and Its Potential as an Important Source of Nutrition, J. of Nutraceuticals, Functional & Medical Foods, 2000, vol. 2(4), p. 35-53.
EP 16 873 619.7 Supplementary Partial European Search Report dated Oct. 9, 2019.

(56) References Cited

OTHER PUBLICATIONS

EP 16 873 618 Supplementary European Search Report dated Nov. 16, 2018.
CN102845568 English Abstract, pp. 1-2; 2013.
Indian Patent Application No. 201647041745, Office Action dated Dec. 17, 2020.
Dalili; et al.; Adding Colchicine to the Antiretroviral Medication—Lopinavir/Ritonavir (Kaletra) in Hospitalized Patients with Non-Severe Covid-19 Pneumonia: A Structured Summary of a Study Protocol for a Randomized Controlled Trial; Published online Jun. 5, 2020; Trials 2020; 21: 489.
Kalepu, et al. Oral Lipid-based drug delivery systems—an overview; Acta PharmaceuticaSinicaB2013;3(6):361-372; 2013.

* cited by examiner

COMPOSITIONS AND METHODS FOR ENHANCED DELIVERY OF ANTIVIRAL AGENTS

FIELD

Disclosed herein are methods, compositions and kits for treating a viral infection, for example, COVID-19, MERS and SARS. The disclosed compositions provide for enhanced delivery of the disclosed antiviral agents.

DETAILED DESCRIPTION OF THE DISCLOSURE

Figure 1:
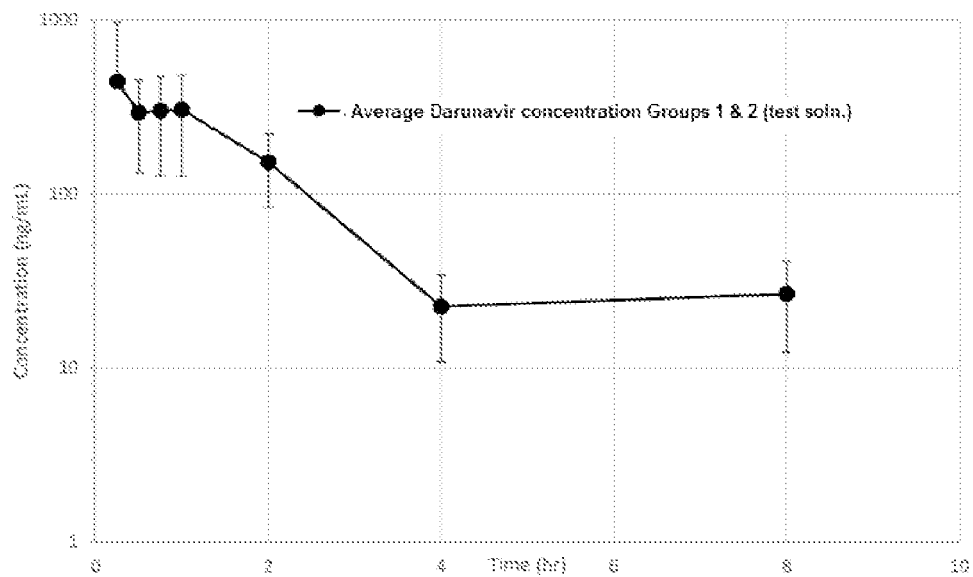
FIG. 1 depicts the average plasma concentration of darunavir in the test animals at 1 hour is approximately 306 ng/mL and at 2 hours is approximately 153 ng/mL.
Figure 2:
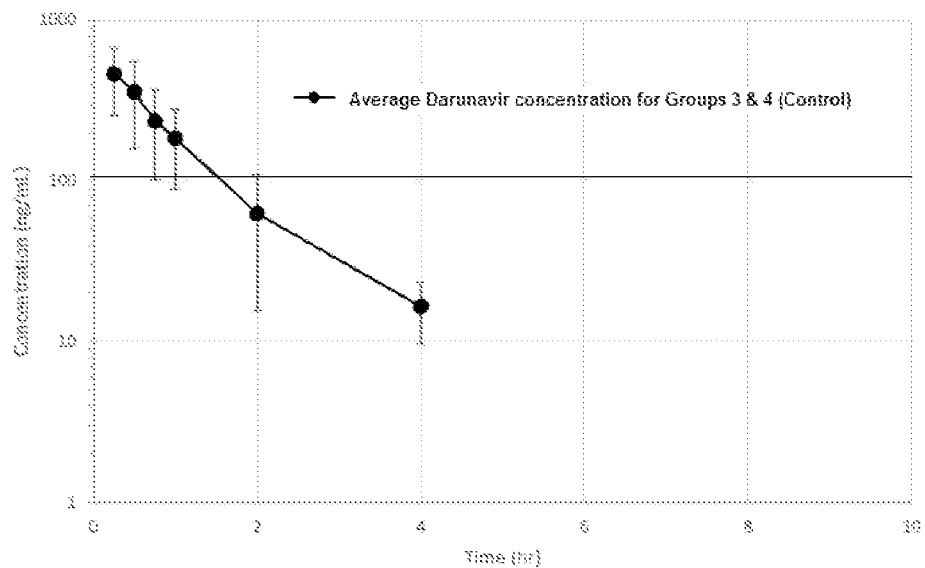
FIG. 2 depicts the average plasma concentration of darunavir in the animals given the control formulation at 1 hour is approximately 185 ng/mL and at 2 hours is approximately 63 ng/mL.

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the disclosed compounds or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

As used herein, the term "Coronaviridae" refers to a family of enveloped, positive-sense, single-stranded RNA viruses. The term "coronavirus" refers in the methods described herein specifically to SARS-CoV-2, which causes COVID-19, and which originated in Wuhan China in 2019. The term coronavirus and variations thereof are used interchangeably throughout the disclosure. Other Coronaviridae viruses are used as examples, targets and standards by which the presently disclosed compounds are measured. For example, MERS (Middle East Respiratory Syndrome) coronavirus.

As used herein, the term "subject" refers to a human or an animal that has been diagnosed with COVID-19 or one or more strains of SARS-CoV-2, or has tested positive for COVID-19 or one or more strains of SARS-CoV-2. The term subject also includes humans or animals that have been exposed to Wuhan coronavirus but are not symptomatic.

As used herein, the term "Lassa virus" refers to a RNA virus belonging to the family of Arenaviridae. As used herein "Lassa fever" refers to an acute viral haemorrhagic illness caused by Lassa virus.

As used herein the term Poxiviridae refers to the poxvirus family. Four genera of poxviruses may infect humans: orthopoxvirus, parapoxvirus, yatapoxvirus, molluscipoxvirus. Orthopox: smallpox virus (variola), vaccinia virus, cowpox virus, monkeypox virus; Parapox: orf virus, pseudocowpox, bovine papular stomatitis virus; Yatapox: tanapox virus, yaba monkey tumor virus; Molluscipox: molluscum contagiosum virus (MCV). The most common are vaccinia (seen on Indian subcontinent) and molluscum contagiosum, but monkeypox infections are rising (seen in west and central African rainforest countries).

As used herein, the term "Vaccinia" refers to a family of large, complex, enveloped virus belonging to the poxvirus family. It is characterized by having a linear double-stranded CAN genome approximately 190 kbp in length, which encodes approximately 250 genes. The dimensions of the virion are roughly 360×270×250 nm, with a mass of about 5-10 fg. Included with in the genus are the species buffalo virus, cantagalo virus, rabbitpox virus Utrecht, Vaccinia virus Ankara, Vaccinia virus Copenhagen and Vaccinia virus WR.

HIV differs from many viruses in that it has very high genetic variability. This diversity is a result of its fast replication cycle, with the generation of about $10^{10}$ virions every day, coupled with a high mutation rate of approximately $3 \times 10^{-5}$ per nucleotide base per cycle of replication and recombinogenic properties of reverse transcriptase.

As used herein then term "Orthomyxoviridae" refers to common "Influenza," for example, illnesses caused by any of three types of Influenza viruses: Type A, Type B, or Type C. Influenza A virus has a large number of subtypes, for example, H1N1, H5N1, H7N9 ("bird flu"), and the like. The viruses are named after the specific combination of hemagglutinin and neuraminidase that comprises the viral package. Because there are 18 known types of hemagglutinin and 11 known types of neuraminidase, in, in theory, 198 different combinations of these proteins are possible. This type of virus is the most common in humans and animals.

As used herein the term Filovirndae refers to a virus family that includes the following genera, including Cuevavirus, Dianlovirus, Ebolavirus and Marburgvirus. Importantly as it relates to Filoviridae, Ebolavirus includes the species Bombali ebolavirus, Bundibugyo ebolavirus, Reston ebolavirus, Sudan ebolavirus, Tai Forest ebolavirus and Zaire ebolavirus. Marburgvirus includes the species Marburg Marburgvirus. These viruses cause viral haemorrhagic fever in humans.

As used herein the term Herpesviridae refers to a family of viruses which includes the following genra found in humans: Cytomegalovirus, Rhadinovirus, Roseolovirus, Simplexvirus, and Lymphocrytovirus. Species of Herpesviridae include Human alphaherpesvirus I and Human alphaherpesvirus 1.

As used herein the term Flavivirdae refers to a family of viruses typically spread via insects, for examples, ticks and mosquitoes. Flaviridae includes the following genra: Flavivirus (Yellow fever, West Nile, Dengue and Zika viruses) and Gepacivirus (hepatitis viruses).

As used herein then term "Orthoretrovirinae" refers to the virus family which includes the Human Immunodeficiency viruses (HIV), for example, the two species of Lentivirus; Human immunodeficiency virus I and Human immunodeficiency virus 2.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant for a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient, to minimize any adverse side effects in the subject, and to optimize formulation for drug delivery and dosing to the target tissues infected by Coronaviridae as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

The terms "composition" and "formulation" are used interchangeably throughout the Specification to refer to the disclosed combination of ingredients which deliver increased plasma level concentrations of anti-viral compounds.

As used herein the term "active base" refers to the two essential components of the disclosed compositions: one or more antiviral agents and a bioavailability enhancing agent. As disclosed herein below, an antiviral agent and a bioavailability enhancing agent can be given to a subject in need without any other active or inactive ingredients present to achieve the desired increase in antiviral plasma levels.

As used herein, the term "unit-dosage form" refers to a physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. A unit-dosage form may be administered in fractions or multiples thereof. Examples of a unit-dosage form include a tablet, liquid formulation or and individually packaged tablet and capsule.

As used herein, the term "multiple-dosage form" is a plurality of identical unit-dosage forms packaged in a single container to be administered in segregated unit-dosage form. Examples of a multiple-dosage form include a bottle of tablets or capsules, or bottle of a liquid composition.

As used herein, and unless otherwise specified, the terms "composition," "formulation," and "dosage form" are intended to encompass products comprising the specified ingredient(s), for example, and antiviral agent, bioavailability agent (in the specified amounts, if indicated), as well as any product(s) which result, directly or indirectly, from combination of the specified ingredient(s) in the specified amount(s).

As disclosed herein the terms "bile acid," "bile salt," "bile acid/salt," "bile acids," "bile salts," and "bile acids/salts" are, unless otherwise indicated, utilized interchangeably herein. Any reference to a bile acid used herein includes reference to a bile acid or a salt thereof. Furthermore, it is to be understood that any singular reference to a component (bile acid or otherwise) used herein includes reference to one and only one, one or more, or at least one of such components. Similarly, any plural reference to a component used herein includes reference to one and only one, one or more, or at least one of such components, unless otherwise noted.

"Test agents" or otherwise "test compounds" as used herein refers to an agent or compound that is to be screened in one or more of the assays described herein. Test agents include compounds of a variety of general types including, but not limited to, small organic molecules, known pharmaceuticals, polypeptides; carbohydrates such as oligosaccharides and polysaccharides; polynucleotides; lipids or phospholipids; fatty acids; steroids; or amino acid analogs. Test agents can be obtained from libraries, such as natural product libraries and combinatorial libraries. In addition, methods of automating assays are known that permit screening of several thousands of compounds in a short period.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

As used herein "stop-gap" refers to the administration of the disclosed compounds to ameliorate the spread of a coronavirus and emergence of drug resistant strains. A stop-gap administration is a temporary measure designed to control the spread of the virus until medical personnel can evaluate the extent of infection and/or the source.

Details associated with the embodiments described above and others are described below.

DETAILED DESCRIPTION

Disclosed herein are compositions or formulations that can deliver antiviral agents in a more effective manner. The disclosed compositions overcome the low bioavailability of known antiviral agents. Bioavailability refers to the extent and rate at which the disclosed antiviral agent enters systemic circulation, thereby accessing the site of action. Bioavailability for a given formulation provides an estimate of the relative fraction of the orally administered dose that is absorbed into the systemic circulation. Low bioavailability is most common with oral dosage forms of poorly water-soluble, slowly absorbed drugs. Insufficient time for absorption in the gastrointestinal tract is a common cause of low bioavailability. If the drug does not dissolve readily or cannot penetrate the epithelial membrane (e.g., in some examples, if it is highly ionized and polar), time at the absorption site may be insufficient. For orally administered drugs, passage through the stomach to the intestinal wall and then the portal circulation to the liver are causes of poor bioavailability. Antiviral agents not well absorbed will undergo first-pass metabolism, for example, glucuronidation, after which the antiviral agent as a metabolite is excreted in the urine or feces. The lack of bioavailability is therefore, due to inadequate absorption.

Bioavailability of an antiviral agent can usually be assessed by determining the area under the plasma concentration-time curve (AUC). AUC is directly proportional to the total amount of unchanged drug that reaches systemic circulation. Plasma drug concentration increases with extent of absorption; the maximum (peak) plasma concentration is reached when drug elimination rate equals absorption rate. Peak time is the most widely used general index of absorption rate; the slower the absorption, the later the peak time.

Antiviral agents can be further administered by delivery to the oral, oropharyngeal, nasal, olfactory, pulmonary and/or genitourinary mucosa, whether intended for systemic perfusion or localized delivery.

Compositions

For the purposes of the present disclosure, the terms "a pharmaceutically effect amount" or "an effective amount" is used interchangeably throughout the Specification. An effective amount is the amount of an antiviral agent that comprises a disclosed composition or formulation and which results in an increase in the plasma concentration of a subject being administered the antiviral agent in a disclosed composition or formulation versus the plasma level of the same antiviral agent administered in a non-disclosed formulation or composition. For example, the study herein below demonstrates the increase in plasma levels of darunavir and efavirenz when administered in a disclosed formulation versus the same drugs administered without the benefit of the disclosed bioavailability agents.

A general aspect of the disclosed compositions relates to the active base, comprising:

a) one or more antiviral agents; and
b) a bioavailability enhancing agent.

In one embodiment of the general aspect of the disclosed compositions relates to the active base, comprising:

a) one or more anti-inflammatory agents; and
b) a bioavailability enhancing agent.

In another embodiment of the general aspect of the disclosed compositions relates to the active base, comprising:

a) one or more antiviral agents and an anti-inflammatory agent; and
b) a bioavailability enhancing agent The administration of the active base without other active or inactive ingredients results in an increase in the plasma concentration of the one or more antiviral agents. The formulator will understand that administration of the antiviral agents and bioavailability enhancing agent will serve to promote increase formulatability, stability, provide options for safe and quantitative delivery, as well as provide a range of options for deliver, for example, via a comestible agent as described herein.

The following aspects relate to the composition of the active base prior to admixing or combining the active base with other ingredients as discussed herein below. In one aspect, the active base can comprise:

a) from about 20% to about 65% by weight of one or more antiviral agents;
b) from about 35% to about 80% by weight of a bioavailability enhancing agent.

In another aspect, the active base can comprise:

a) from about 30% to about 60% by weight of one or more antiviral agents;
b) from about 40% to about 70% by weight of a bioavailability enhancing agent.

In a further aspect, the active base can comprise:

a) from about 20% to about 50% by weight of one or more antiviral agents;
b) from about 50% to about 80% by weight of a bioavailability enhancing agent.

In still further aspect, the active base can comprise:

a) from about 33% to about 67% by weight of one or more antiviral agents;
b) from about 33% to about 67% by weight of a bioavailability enhancing agent.

In still yet further aspect, the active base can comprise:
a) from about 33% to about 50% by weight of one or more antiviral agents;
b) from about 50% to about 67% by weight of a bioavailability enhancing agent.

The disclosed active base can comprise from about 20% to about 65% by weight of one or more antiviral agents. For example, 20%, 21%, 22%, 23%, 24%, 25%, 26%, 27%, 28%, 29%, 30% 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% by weight of one or more antiviral agents.

The disclosed active base can comprise from about 20% to about 65% by weight of one or more bioavailability enhancing agents. For example, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80% by weight of a bioavailability enhancing agent.

The formulator will recognize that the same increase in plasma level concentration cannot be expected from one antiviral agent to the next. An increase can be expected when a particular antiviral agent is formulated as disclosed herein versus a composition that does not comprise the ingredients disclosed herein.

Antiviral Agents

The disclosed antiviral agent can be chosen from protease inhibitors, endonuclease inhibitors, integrase inhibitors, enzyme inhibitors, non-nucleoside reverse transcriptase inhibitors, fusion inhibitors, cell entry inhibitors, mRNA and protein synthesis inhibitors cannabinoids, viral replication blockers, uncoating inhibitors, reverse transcriptase inhibitors, topoisomerase inhibitors, assembly inhibitors, M2 inhibitors, DNA polymerase inhibitors, DNA terminase complex inhibitors, HCV protein inhibitors, neuraminidase inhibitors, virus-neutralizing antibodies, and the like.

One aspect of the present disclosure relates to the delivery of protease inhibitors. Non-limiting examples of protease inhibitors include amprenavir (or the pro-drug fosamprenavir), atazanavir, bepridil, boceprevir, darunavir, ebastine, indinavir, lopinavir, nelfinavir, ritonavir, rupintrivir, saquinavir, simeprevir, telaprevir, and tipranavir.

A further aspect relates to the delivery of Nucleoside Reverse Transcriptase Inhibitors (NNRTI). Non-limiting examples of NNRTI antiviral agents include doravirine, efavirenz, etravirine, loviride, and rilpivirine.

Other suitable antiviral agents include liver enzyme inhibitors, for example, cobicistat; endonuclease inhibitors, for example, baloxavir marboxil; integrase inhibitors, for example, bictegravir and elvitegravir; HCV protein inhibitors, for example, daclatasvir; fusion/entry inhibitors, for example, maraviroc and umifenovir; cell entry prohibitors, for example, colchicine; mRNA synthesis inhibitors, for example, methisazone; tromantadine, which prevents viral DNA replication, prevents viral uncoating, prevents viral entry; and replication inhibitors, for example rimantadine.

Other antiviral compounds include GS-441524 ((1R,2R,3R,4R,5S)-2-(4-aminopyrrolo[2,1-f][1,2,4]triazin-7-yl)-4,5-dihydroxy-3-(hydroxymethyl)cyclopentane-carbonitrile) having the formula:

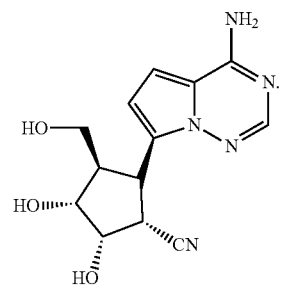

GS-441524 is the precursor nucleotide to remdesivir having the formula:

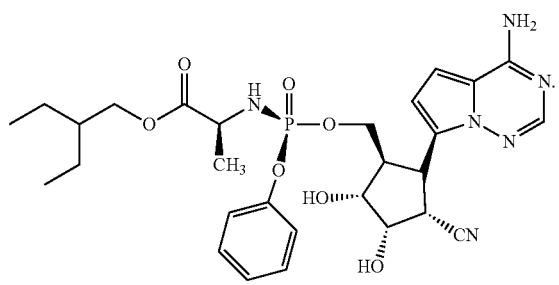

Remdesivir is an investigational intravenous drug with broad antiviral activity that inhibits viral replication through premature termination of RNA transcription and has in vitro activity against SARS-CoV-2 and in vitro and in vivo activity against related betacoronaviruses.

In addition to antivirus agents, virus neutralizing, fully human antibodies, for example, sarilumab can be used in the disclosed compositions, alone or in combination with the disclosed antiviral agents.

Other non-limiting examples of antiviral agents includes chloroquine (See, Wang M et al., "Remdesivir and chloroquine effectively inhibit the recently emerged novel coronavirus (2019-nCoV) in vitro," *Cell Research* 30, 269-271 (2020)) and hydroxy-chloroquine. Hydroxychloroquine and chloroquine are oral prescription drugs that have been used for treatment of malaria and certain inflammatory conditions. Hydroxy-chloroquine and chloroquine are under investigation in clinical trials for pre-exposure or post-exposure prophylaxis of SARS-CoV-2 infection, and treatment of patients with mild, moderate, and severe COVID-19.

The following are non-limiting examples of antivirals or compounds used to treat Covid-19 or that are directed to the treatment of HIV.

Indinavir

HIV-1 protease is an enzyme required for the proteolytic cleavage of the viral polyprotein precursors into the individual functional proteins found in infectious HIV-1. This compound binds to the protease active site and inhibits the activity of the enzyme. As such, indinavir acts to regulate HIV by inhibiting the virus' critical protease activity.

Raltegravir

Raltegravir in an integrase inhibitor. As such, raltegravir acts to regulate a key enzyme in the replication mechanism of HIV. The HIV integrase is responsible for the transfer of virally encoded DNA into the host chromosome which is a necessary event in retroviral replication.

Nevirapine

Nevirapine is a non-nucleoside reverse transcriptase inhibitor (NNRTI) of HIV-1 which blocks HIV-1 RNA-dependent and DNA-dependent DNA polymerase activities by causing a disruption of the enzyme's catalytic site. Nevirapine does this by binding directly to the reverse transcriptase (RT).

Azidothymidine (AZT)

AZT, a thymidine analogue, works by selectively inhibiting HIV's reverse transcriptase, the enzyme that the virus uses to make a DNA copy of its RNA. Thus AZT inhibits HIV replication without affecting the function of uninfected cells.

Colchicine

In addition to antiviral agents, anti-inflammatory agents can be used to treat viral infections either alone or in combination with antiviral agents. For example, colchicine which has the formula:

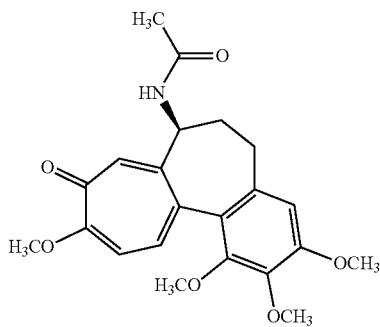 [SMILES: COc1cc2c(c(OC)c1OC)-c1ccc(OC)c(=O)cc1[C@@H](NC(C)=O)CC2]

Colchicine is used to treat inflammatory disorders. It is known to work via several mechanisms including reducing Intereukin-6, Interleukin-8, Tumour Necrosis Factor-alpha. Recently it has been prescribed to control the oxidative stress pathways which is an important component in the clinical course and outcome of patients infected with COVID-19. See Dalili N et al., "Adding Colchicine to the antiretroviral Medication—Lopinavir/Ritonavir (Kaletra) in Hospitalized Patients with Non-Severe Covid-19 Pneumonia: A structured Summary of a Study Protocol for a Randomized Controlled Trial," Trials, 21: 489 (2020). (https://www.ncbi.nlm.nih.gov/pmc/articles/PMC7367785).

The disclosed compositions can comprise from about 25 mg to about 300 mg. In one aspect the disclosed single dose compositions of a disclosed antiviral agent can comprise any amount from about 25 mg to about 200 mg.

In a further aspect the disclosed single dose compositions of a disclosed antiviral agent can comprise any amount from about 100 mg to about 200 mg. In a yet further aspect the disclosed single dose compositions of a disclosed antiviral agent can comprise any amount from about 75 mg to about 250 mg. In another further aspect the disclosed single dose compositions of a disclosed antiviral agent can comprise any amount from about 50 mg to about 150 mg. In a yet another aspect the disclosed single dose compositions of a disclosed antiviral agent can comprise any amount from about 100 mg to about 200 mg. In a yet still further aspect the disclosed single dose compositions of a disclosed antiviral agent can comprise any amount from about 200 mg to about 300 mg.

The disclosed compositions can comprise any amount of antiviral agent from about 25 mg to about 300 mg. For example, the disclosed compositions can comprise 25 mg, 26 mg, 27 mg, 28 mg, 29 mg, 30 mg 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 190 mg, 191 mg, 192 mg, 193 mg, 194 mg, 195 mg, 196 mg, 197 mg, 198 mg, 199 mg, 200 mg, 201 mg, 202, mg, 203, mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, or 300 mg of one or more antiviral agents.

The disclosed compositions can provide a single dose of a disclosed antiviral agent based upon the body mass of the subject being treated. Therefore, a single dose of a disclosed antiviral agent can range from about 0.35 mg/kg to about 20 mg/kg of the subject's body mass.

In one embodiment, the amount of a disclosed antiviral agent in a single dose is from about 1 mg/kg to about 8 mg/kg of the subject's body mass.

In another embodiment, the amount of a disclosed antiviral agent in a single dose is from about 2 mg/kg to about 5 mg/kg of the subject's body mass.

In a further embodiment, the amount of a disclosed antiviral agent in a single dose is from about 1.5 mg/kg to about 4 mg/kg of the subject's body mass.

In a yet further embodiment, the amount of a disclosed antiviral agent in a single dose is from about 4 mg/kg to about 10 mg/kg of the subject's body mass.

In a still further embodiment, the amount of a disclosed antiviral agent in a single dose is from about 5 mg/kg to about 8 mg/kg of the subject's body mass.

For example, the dose can comprise any amount from about 0.5 mg/kg to about 10 mg/kg on the body mass of the subject being treated.

For example, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, or 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 90 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or 10.0 mg/kg of body mass.

Pharmaceutically Acceptable Salts

In some embodiments of the disclosed compositions, the antiviral agent is in the form of a pharmaceutically acceptable salt. Non-limiting examples of pharmaceutically acceptable salts include acetate, adipate, alginate, aspartate, benzoate, benzenesulfonate (besylate), bisulfate, butyrate, citrate, camphorate, camphorsulfonate, cyclopentane-propionate, digluconate, dodecylsulfate, 1,2-ethanedisulfonate (edisylate), ethanesulfonate (esylate), formate, fumarate, glucoheptanoate, glycerophosphate, glycolate, hemisulfate, heptanoate, hexanoate, hydrochloride, hydrobromide, hydroiodide, 2-hydroxyethane-sulfonate, lactate, maleate, malonate, methanesulfonate (mesylate), 2-naphthalene-sulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

Bioavailability Enhancing Agent

The disclosed bioavailability enhancing agent comprises one or more triglycerides. In one aspect the disclosed triglycerides are edible oils. An edible oil is defined herein as an oil that is capable of undergoing de-esterification or hydrolysis in the presence of pancreatic lipase in vivo under normal physiological conditions. Specifically, digestible oils comprise glycerol triesters of $C_6$-$C_{22}$ fatty acids. The term "edible oil" refers to oils derived from plants, for example, corn oil, sunflower oil, oils derived from living animals, for example, fish oils. In addition, the oils can be derived from krill.

The disclosed edible oils can have a low percentage of saturated fatty acids, for example, hemp seed oil (7.0%) or a high percentage of saturated fatty acids, for example, coconut oil (82.5%) provided the solid content index is such that the oil is liquid and flowable at temperatures above about 15° C.

In one aspect of the disclosed bioavailability enhancing agents the triglycerides comprise less than or equal to about 5% by weight of free fatty acids, mono-glycerides and di-glycerides. The triglycerides of the disclosed bioavailability enhancing agent are refined, bleached and de-odorized.

Vegetable oils comprise the disclosed triglycerides. These oils are refined in order to remove the non-glyceride impurities that are present in the crude oil. Some of these impurities are naturally present in the seeds or formed during harvesting and storage of seeds or during extraction of crude oil and subsequently during its refining. Oil refining processes for vegetable oils are designed to remove these impurities from the oil or reduce them to a level where their deleterious effects on oil stability are minimal and made suitable for human consumption or for pharmaceutical formulation. Vegetable oil undergoes degradation almost immediately after the seed is crushed. The oil starts to show the signs of primary oxidation as measured by its peroxide value. Under certain circumstances the oil may develop a darker color or higher free fatty acids and eventually an unpleasant odor or viscosity. Gums, phosphatides and mucilaginous substances act as emulsifiers increasing loss of oil and can decompose at processing temperatures. Free fatty acids increase foaming and diminish the storage and formulating properties of the disclosed oils.

Presence of compounds such as phosphatides, free fatty acids, odiferous volatiles, colourant, waxes and metal compounds in oil negatively affect the desired properties for compounding with the disclosed antiviral compounds and storage stability of the refined oil avoids the presence of any unwanted or reactive species being a part of the final composition. Refining processes have, therefore, been developed to remove undesirable compounds such as tocopherols, phenols, sterols and the like.

Chemical refining includes degumming, neutralizing, bleaching, winterizing and de-odorizing stages. The edible oils of the disclosed bioavailability enhancing agents are refined oils that have been winterized to prevent the precipitation of wax.

The disclosed oils are refined, bleached and deodorized to obtain as complete a pure triglyceride composition. There will be, however, some amount of mono- and diglycerides present in the final oil. Some of the disclosed oils can be obtained from the host plant by supercritical extraction or other harvesting means. The final oils used in the disclosed formulations comprise at least about 97% by weight of triglycerides and the balance compatible ingredients, inter alia, mono- and diglycerides and free fatty acids or fatty acid esters, phosphatides, sterols, fatty alcohols, fat soluble vitamins and other color bodies.

Disclosed herein are non-limiting examples of edible oils suitable for use in delivering antiviral agents. Plant based oils include borage seed oil, syzigium aromaticum oil, hempseed oil, herring oil, cod-liver oil, salmon oil, flaxseed oil, wheat germ oil, evening primrose oils, almond oil, babassu oil, borage oil, black currant seed oil, canola oil, castor oil, coconut oil, corn oil, cottonseed oil, emu oil, evening primrose oil, flax seed oil, grapeseed oil, groundnut oil (e.g., peanut), lanolin oil, linseed oil, mink oil, mustard seed oil, olive oil, palm oil, palm kernel oil, rapeseed oil, safflower oil, sesame oil, shark liver oil, soybean oil, sunflower oil, tree nut oil, hydrogenated castor oil, hydrogenated coconut oil, hydrogenated palm oil, hydrogenated soybean oil, hydrogenated vegetable oil, glyceryl trioleate, glyceryl trilinoleate, glyceryl trilinolenate, citrate thisocetyl triglyceride having 10-18 carbon atoms, omega-3 polyunsaturated fatty acid triglyceride containing oil, omega-3 oil, omega-6 oil, and any combination thereof.

In one embodiment the edible oil is chosen from palm kernel oil, soybean oil, rapeseed oil (canola), sunflower oil, groundnut oil, sesame oil, flaxseed oil, palm oil, olive oil and corn oil. In one iteration, the edible oil is chosen from soybean oil, rapeseed oil (canola), sunflower oil, palm oil, olive oil or corn oil. A non-limiting example of an edible oil used in the disclosed formulations includes sunflower oil. A further non-limiting example of an edible oil used in the disclosed formulations includes palm oil. A still further non-limiting example of an edible oil used in the disclosed formulations includes rapeseed oil. A yet still further non-limiting example of an edible oil used in the disclosed formulations includes soybean oil. A further non-limiting example of an edible oil used in the disclosed formulations includes corn oil.

In one aspect the edible oils comprise one or more fish oils. Included within fish oil are algal oils. Non-limiting examples of fish oils include herring, sardines, Spanish mackerel, salmon, halibut, tuna, swordfish, tilefish, pollock, cod, catfish, flounder, grouper mahi mahi, orange roughy, red snapper, shark, king mackerel, hoki, and gemfish.

Edible oils having a plurality of non-conjugated di-enes and tri-enes, for example, linoleic and linolenic acids, can by "touch hardened" to increase the amount of mono-olefins present. Touch harden refers to hydrogenation to a point wherein the Iodine value of the triglyceride is lowered to I-107 or less.

The disclosed compositions can comprise from about 50 mg to about 600 mg. In one aspect the disclosed single dose compositions of a disclosed bioavailability enhancing agent can comprise any amount from about 50 mg to about 400 mg.

In a further aspect the disclosed single dose compositions of a disclosed bioavailability enhancing agent can comprise any amount from about 100 mg to about 200 mg. In a yet further aspect the disclosed single dose compositions of a disclosed bioavailability enhancing agent can comprise any amount from about 150 mg to about 250 mg. In a still further aspect the disclosed single dose compositions of a disclosed bioavailability enhancing agent can comprise any amount from about 200 mg to about 400 mg The disclosed single dose compositions can comprise any amount a disclosed bioavailability enhancing agent from about 50 mg to about 600 mg. For example, the disclosed compositions can comprise 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 190 mg, 191 mg, 192 mg, 193 mg, 194 mg, 195 mg, 196 mg, 197 mg, 198 mg, 199 mg, 200 mg, 201 mg, 202, mg, 203, mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 301 mg, 302, mg, 303, mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 323 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 390 mg, 391 mg, 392 mg, 393 mg, 394 mg, 395 mg, 396 mg, 397 mg, 398 mg, 399 mg, 400 mg, 401 mg, 402, mg, 403, mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 440 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 490 mg, 491 mg, 492 mg, 493 mg, 494 mg, 495 mg, 496 mg, 497 mg, 498 mg, 499 mg, 500 mg, 501 mg, 50 q, mg, 503, mg, 504 mg, 505 mg, 506 mg, 507 mg, 508 mg, 509 mg, 510 mg, 511 mg, 51 q mg, 513 mg, 514 mg, 515 mg, 516 mg, 517 mg, 518 mg, 519 mg, 520 mg, 551 mg, 525 mg, 553 mg, 554 mg, 555 mg, 556 mg, 557 mg, 558 mg, 559 mg, 530 mg, 531 mg, 532 mg, 533 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, 550 mg, 551 mg, 552 mg, 553 mg, 554 mg, 555 mg, 556 mg, 557 mg, 558 mg, 559 mg, 560 mg, 561 mg, 562 mg, 563 mg, 564 mg, 565 mg, 566 mg, 567 mg, 568 mg, 569 mg, 570 mg, 571 mg, 572 mg, 573 mg, 574 mg, 575 mg, 576 mg, 577 mg, 578 mg, 579 mg, 580 mg, 581 mg, 582 mg, 583 mg, 584 mg, 585 mg, 586 mg, 587 mg, 588 mg, 589 mg, 590 mg, 590 mg, 591 mg, 592 mg, 593 mg, 594 mg, 595 mg, 596 mg, 597 mg, 598 mg, 599 mg, or 600 mg of one or more bioavailability enhancing agents.

Adjunct Ingredients

The disclosed compositions can comprise one or more adjunct ingredients.

Emulsifiers

The disclosed compositions can comprise from about 30% to about 80% one or more emulsifiers. Non-limiting examples of emulsifiers are chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof.

The disclosed compositions can comprise an emulsifier system comprising an emulsifier and a solubilizing carrier. For example:

i) an emulsifier; and
ii) a carrier.

Typically, after addition of the active base and emulsifier, one or more components may remain not fully dissolved. In that case the formulator can add a carrier to achieve composition homogeneity.

For example:

i) from about 85% to about 95% an emulsifier; and
ii) from about 5% to about 15 a carrier.

In one embodiment the compositions comprise from about 30% to about 80% of one or more emulsifiers. In another embodiment the compositions comprise from about 60% to about 80% of one or more emulsifiers. In a further embodiment the compositions comprise from about 50% to about 70% of one or more emulsifiers. In in a yet another embodiment the compositions comprise from about 60% to about 70% of one or more emulsifiers. In a still further embodiment the compositions comprise from about 40% to about 70% of one or more emulsifiers. In a still yet further embodiment the compositions comprise from about 35% to about 80% of one or more emulsifiers.

The compositions can comprise any amount of emulsifier from 30% to 80%, for example, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80%.

Bile Salts

The disclosed compositions can comprise from about 1% to about 15% of one or more bile salts. The bile salts enhance the ability of the disclosed compositions to target the duodenum. Non-limiting examples of bile salts and/or bile acids includes steroid acids (and/or the carboxylate anion thereof) and salts thereof, found in the bile of an animal (e.g., a human), including cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, lithocolate, and the like. Taurocholic acid and/or taurocholate are referred to herein as TCA.

Bile salts are typically conjugated with glycine or taurine. For example, the term "bile acid" as used herein includes cholic acid conjugated with either glycine or taurine: glycocholate and taurocholate, respectively (and salts thereof). Any reference to a bile salt or bile acid used herein includes reference to an identical compound naturally or synthetically prepared.

In one embodiment the composition comprises from about 3% to about 12% of a bile salt. In another embodiment the composition comprises from about 5% to about 12% of a bile salt. In a further embodiment the composition comprises from about 7% to about 12% of a bile salt. In a still further embodiment the composition comprises from about 7% to about 15% of a bile salt. In in a yet further embodiment the composition comprises from about 8% to about 15% of a bile salt. The compositions can comprise, for example, 1%, 2%, 3%, 4%, 5%, 6%, 7%, 8%, 9%, 10%, 11%, 12%, 13%, 14%, or 15% of one or more bile salts. In one non-limiting example the bile used herein is ox bile.

Carriers

The disclosed compositions can comprise from about 1% to about 10% by weight of one or more pharmaceutically acceptable carriers. In one embodiment the compositions comprise from about 1% to about 5% of a carrier. In another embodiment the compositions comprise from about 1% to about 4% of a carrier. In further embodiment the compositions comprise from about 3% to about 7% of a carrier. In a yet further embodiment the compositions comprise from about 4% to about 8% of a carrier. In a still further embodiment the compositions comprise from about 6% to about 10% of a carrier. The compositions can comprise, for example, 1%, 2%, 3%, 4%, 5%, 6%, 7%, 8%, 9%, or 10% of one or more carriers.

The term "pharmaceutically acceptable carrier" refers to a diluent, adjuvant or excipient, with which the disclosed compositions can be admixed or otherwise delivered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof Except insofar as any conventional carrier medium is incompatible with the compounds of the disclosure such as by producing any undesirable biological effect or otherwise interacting in a deleterious manner with any other component(s) of the pharmaceutically acceptable composition, its use is contemplated to be within the scope of this disclosure. Examples of pharmaceutically acceptable carriers include, but are not limited to buffer substances such as phosphates, glycine, sorbic acid, or potassium sorbate, partial glyceride mixtures of saturated vegetable fatty acids, water, sugars such as lactose, glucose and sucrose; starches such as corn starch and potato starch; cellulose and its derivatives such as sodium carboxymethyl cellulose, ethyl cellulose and cellulose acetate.

Non-limiting examples of carriers includes water, ethanol, glycerin, propylene glycol, and sorbitol.

Surfactants

The disclosed compositions can comprise from about 1% to about 15% one or more surfactants. In one embodiment the composition comprises from about 3% to about 12% of a surfactant. In another embodiment the composition comprises from about 5% to about 12% of a surfactant. In a further embodiment the composition comprises from about 7% to about 12% of a surfactant. In a still further embodiment the composition comprises from about 7% to about 15% of a surfactant. In in a yet further embodiment the composition comprises from about 8% to about 15% of a surfactant. The compositions can comprise, for example, 1%, 2%, 3%, 4%, 5%, 6%, 7%, 8%, 9%, 10%, 11%, 12%, 13%, 14%, or 15% of one or more surfactants.

The following are non-limiting examples of surfactants.

Natural Extract Surfactants

One category of suitable surfactants includes compounds that are extracted from plant material that have surfactant activity. The compositions can comprise from about 0.05% to about 0.5% by weight of one or more natural surfactants. Non-limiting examples include extracts of *Gynostemma pentapphyllum, Panax Ginseng, Sapindus mukorossi, Cucumis sativus, Olea europea*, and the like. Also suitable for use are mixtures of extracts having surfactant properties.

Anionic Surfactants

The disclosed compositions can comprise one or more $C_{10}$-$C_{18}$ alkyl alkoxy sulfates having the formula:

$$CH_3(CH_2)_x(OCH_2CH_2)_yOSO_3M$$

wherein the index x is from 9 to 17, y is from 1 to 7 and M is a water soluble cation chosen from ammonium, lithium, sodium, potassium and mixtures thereof. A non-limiting example includes sodium dodecyl diethoxy sulfate having the formula:

$$CH_3(CH_2)_{11}(OCH_2CH_2)_2OSO_3Na.$$

Alkyl alkoxy sulfates are also commercially available as a mixture of ethoxylates, for example, sodium laureth sulfate is available as a mixture of ethoxylates, i.e., the index y is from 2 to 4. Other suitable examples include sodium laureth-2 sulfate having an average of 2 ethoxylates and a $C_{12}$ linear alkyl chain. Sodium laureth-2 is available as Texapon™ N 56 from Cognis Corp. Further examples of alkyl alkoxy sulfates includes sodium laureth-1 sulfate, sodium laureth-3 sulfate, sodium laureth-4 sulfate, sodium myreth-2 sulfate and sodium myreth-3 sulfate.

The disclosed compositions can comprise one or more $C_{10}$-$C_{18}$ alkyl alkoxy carboxylates having the formula:

$$CH_3(CH_2)_x(OCH_2CH_2)_yCO_2M$$

wherein the index x is from 9 to 17, y is from 1 to 5 and M is a water soluble cation chosen from ammonium, lithium, sodium, potassium and mixtures thereof. A non-limiting example includes sodium dodecyl diethoxy carboxylate having the formula:

$$CH_3(CH_2)_{11}(OCH_2CH_2)_2CO_2Na.$$

Alkyl alkoxy carboxylates are also commercially available as a mixture of ethoxylates, for example, sodium laureth sulfate is available as a mixture of ethoxylates, i.e., the index y is from 2 to 4. Other suitable examples include sodium laureth-2 sulfate having an average of 2 ethoxylates and a $C_{12}$ linear alkyl chain. Sodium laureth-2 is available as Texapon™ N 56 from Cognis Corp. Further examples of alkyl alkoxy sulfates include sodium laureth-1 sulfate, sodium laureth-3 sulfate, sodium laureth-4 sulfate, sodium myreth-2 sulfate and sodium myreth-3 sulfate.

The disclosed compositions can comprise one or more $C_{10}$-$C_{18}$ isethionate esters of alkyl alkoxy carboxylates having the formula:

$$CH_3(CH_2)_x(OCH_2CH_2)_yOCH_2C(O)OCH_2CH_2SO_3M$$

wherein the index x is from 9 to 17, the index y is from 1 to 5 and M is a water soluble cation. Isethionate esters of alkyl alkoxy carboxylates are described in U.S. Pat. No. 5,466,396 the disclosure of which is included herein by reference in its entirety.

The disclosed compositions can comprise one or more $C_{10}$-$C_{18}$ alkyl carboxyamides having the formula:

$$CH_3(CH_2)_xC(O)NR(CH_2)_yCO_2M$$

wherein R is hydrogen or methyl the index x is from 9 to 17, the index y is from 1 to 5 and M is a water soluble cation. A non-limiting example of an alkyl carboxyamide suitable for use in the disclosed compositions includes potassium cocoyl glycinate available as AMILITE™ GCK-12 from Ajinomoto. A further example includes compounds wherein R is methyl, for example, sodium cocoyl sarcosinate.

Zwitterionic Surfactants

One category of zwitterionic surfactants relates to $C_{10}$-$C_{16}$ alkyl amide betaines having the formula:

$$CH_3(CH_2)_wC(O)NH(CH_2)_uN^+(CH_3)_2(CH_2)_tCO_2^-$$

wherein the index w is from 9 to 15, the index u is from 1 to 5 and the index t is from 1 to 5.

Non-limiting examples of betaine surfactants includes {[3-(decanoylamino)ethyl]-(dimethyl)-ammonio}acetate, {[3-(decanoylamino)ethyl](dimethyl)ammonio}-acetate, {[3-(dodecanoyl-amino)ethyl](dimethyl)ammonio}acetate, {[3-(dodecanoylamino)propyl]-(dimethyl)-ammonio}acetate, {[3-(dodecanoylamino)-butyl](dimethyl)ammonio}acetate, {[3-(tetra-decanoylamino)ethyl](dimethyl)-ammonio}acetate, {[3-(tertadecanoylamino)-propyl](dimethyl)ammonio}acetate, {[3-(hexadecanoylamino)ethyl](dimethyl)-ammonio}acetate, and {[3-(hexadecanoylamino)propyl](dimethyl)ammonio}acetate.

Another category of zwitterionic surfactants relates to $C_{10}$-$C_{16}$ alkyl amide sultaines having the formula:

$$CH_3(CH_2)_wC(O)NH(CH_2)_uN^+(CH_3)_2(CH_2)_tSO_3^-$$

wherein the index w is from 9 to 15, the index u is from 1 to 5 and the index t is from 1 to 5. Non-limiting examples of sultaine surfactants includes {[3-(decanoylamino)ethyl]-(dimethyl)-ammonio}methanesulfonate, {[3-(decanoylamino)ethyl](dimethyl)ammonio}-methanesulfonate, {[3-(dodecanoyl-amino)ethyl](dimethyl)ammonio}methanesulfonate, {[3-(dodecanoylamino)-propyl](dimethyl)ammonio}methanesulfonate, {[3-(dodecanoyl-amino)butyl](dimethyl)-ammonio}methanesulfonate, {[3-(tetradecanoylamino)ethyl]-(dimethyl)ammonio}methane-sulfonate, {[3-(tertadecanoylamino)propyl](dimethyl)-ammonio}methanesulfonate, {[3-(hexadecanoylamino)ethyl](dimethyl)ammonio}-methanesulfonate, and{[3-(hexadecanoylamino)propyl](dimethyl)ammonio}-methanesulfonate.

A further category of zwitterionic surfactants relates to $C_{10}$-$C_{16}$ alkyl hydroxy sultaines having the formula:

$$CH_3(CH_2)_wN^+(CH_3)_2CH_2CHOHCH_2SO_3^-$$

wherein the index w is from 9 to 15. Non-limiting examples of alkyl hydroxy sultaine surfactants includes 3-[dodecyl(dimethyl)azaniumyl]-2-hydroxypropane-1-sulfonate (lauryl hydroxysultaine), 3-[tetradecyl(dimethyl)azaniumyl]-2-hydroxypropane-1-sulfonate (myristyl hydroxysultaine), (Z)-{dimethyl[3-(octadec9-enamido)propyl]ammonio}-methanesulfonate (oleyl hydroxysultaine), and the like.

Nonionic Surfactants

One category of nonionic surfactants relates to $C_8$-$C_{18}$ alkylglycosidyl nonionic surfactant having the formula:

$$CH_3(CH_2)_qO[G]_pH$$

wherein G represents a monosaccharide residue chosen from glucose, fructose, mannose, galactose, talose, allose, altrose, idose, arabinose, xylose, lyxose, ribose and mixtures thereof, the index p is from 1 to 4, the index q is from 7 to 17. The following are non-limiting examples of alkyl glucoside surfactants include (2R,3S,4S,5R,6R)-2-(hydroxymethyl)-6-octooxyoxane-3,4,5-triol (octyl glucoside, n-octyl-β-D-glucoside), (2R,3R,4S,5S,6R)-2-decoxy-6-(hydroxymethyl)tetra-hydropyran-3,4,5-triol (decyl glucoside, n-decyl-β-D-glucoside), and (2R,3R,4S,5S,6R)-2-dodecoxy-6-(hydroxymethyl)tetrahydropyran-3,4,5-triol (dodecyl glucoside, lauryl glucoside, n-dodecyl-β-D-glucoside). One example of a suitable admixture of $C_8$-

$C_{16}$ alkylglycosidyl nonionic surfactants is PLANTACARE™ 818 UP available from Cogins Chemical Co.

A further category of nonionic surfactants relates to polyoxyethylene glycol alkyl ethers having the formula:

$$RO(CH_2CH_2O)_nH$$

wherein R is a linear or branched alkyl group having from 6 to 20 carbon atoms and n is an integer of about 2 to about 20.

On example of suitable ethoxylate alcohol surfactants are the NEODOL™ ethoxylated alcohols from Shell Chemicals. NEODOL™ 23-1 is a surfactant comprising a mixture of R units that are $C_{12}$ and $C_{13}$ in length with an average of 1 ethoxy unit. Non-limiting examples of ethoxylated alcohols include NEODOL™ 23-1, NEODOL™ 23-2, NEODOL™ 23-6.5, NEODOL™ 25-3, NEODOL™ 25-5, NEODOL™ 25-7, NEODOL™ 25-9, PLURONIC™ 12R3, and PLURONIC™ 25R2 available from BASF.

A still further category of nonionic surfactants relates to polyoxyethylene glycol alkyl ethers having the formula:

$$RO(CH_2CH(CH_3)O)_nH$$

wherein R is a linear or branched alkyl group having from 6 to 20 carbon atoms and n is an integer of about 2 to about 20.

Another category of nonionic surfactants suitable for use in the disclosed compositions includes polyoxyethylene polyoxypropylene block copolymers known as "poloxamers" having the formula:

$$HO(CH_2CH_2)_{y1}(CH_2CH_2CH_2O)_{y2}(CH_2CH_2O)_{y3}OH$$

these are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. These extracellular desiccants are also well known by the trade name PLURONICS™. These compounds are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units. This category of nonionic surfactant is commercially, for example, under the trade name LUTROL™ F-17 available from BASF.

Another category of adjunct ingredients includes flavor enhancing agents. Non-limiting examples of flavor enhancing agents include vanilla, vanillin, ethyl vanillin, orange oil, lemon oil, peppermint oil, strawberry, raspberry, and mixtures thereof.

Another example of an adjunct ingredient is an emulsifier which provides a homogeneous composition. Non-limiting examples of emulsifiers includes soy and egg lecithin, mono- and diglycerides, polysorbates, carrageenan, and guar gum. In some embodiments one or more of the bioavailability agents can serve a suitable emulsifier.

The disclosed compositions can further comprise lipid soluble vitamins and vitamin precursors. For example, retinol, retinoic acid, β-carotene, cholecalciferol, tocopherols, and vitamin K.

The disclosed compositions can also comprise one or more alkalizing agents to improve intestinal motility. Non-limiting examples include extract of *Cynara cardunculus*, extract of *Zingiber officinale*, cholagogues, sodium carbonate, sodium bicarbonate, as well as other alkaline buffers.

The disclosed compositions can comprise one or more anti-inflammatory drugs or agents with anti-inflammatory properties to reduce the immunological cascade effect associated with viral infections. For example, aspirin, ibuprofen, naproxen, ketoprofen, tolmetin, etodolac, diclofenac, piroxicam, indomethacin or cannabinoids with anti-inflammatory properties such as cannabidiol, cannabinol or others.

The disclosed compositions can comprise one or more anti-caking agents

Compositions

One aspect of the disclosed compositions, comprises:
a) one or more active agents;
b) a bioavailability enhancing agent; and
c) an emulsifier.

In one iteration of this aspect, the compositions comprises:
a) an effective amount of one or more antiviral agents; and
b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof.

In one embodiment of this iteration, the composition comprises:
a) an effective amount of one or more protease inhibitors chosen from amprenavir (or the pro-drug fosamprenavir), bepridil, atazanavir, boceprevir, darunavir, indinavir, lopinavir, nelfinavir, ritonavir, saquinavir, simeprevir, telaprevir, or tipranavir;
b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof.

In another embodiment of this iteration, the composition comprises:
- a) an effective amount of protease inhibitors chosen from amprenavir (or the pro-drug fosamprenavir), bepridil, atazanavir, boceprevir, darunavir, indinavir, lopinavir, nelfinavir, ritonavir, saquinavir, simeprevir, telaprevir, or tipranavir;
- b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
- c) gum arabic.

In one non-limiting example of this embodiment, the composition comprises:
- i) from about 5% to about 20% by weight of an active base, comprising:
  - a) from about 25% to about 50% by weight of darunavir;
  - b) from about 50% to about 75% by weight of sunflower oil; and
- ii) from about 50% to about 70% gum arabic;
- iii) the balance carriers and other adjunct ingredients.

In another non-limiting example of this embodiment, the composition comprises:
- i) from about 1% to about 15% by weight of an active base, comprising:
  - a) from about 25% to about 50% by weight of bepridil;
  - b) from about 50% to about 75% by weight of sunflower oil; and
- ii) from about 50% to about 70% gum arabic.

In a further non-limiting example of this embodiment, the composition comprises:
- i) from about 1% to about 15% by weight of an active base, comprising:
  - a) from about 25% to about 50% by weight of rupintrivir;
  - b) from about 50% to about 75% by weight of sunflower oil; and
- ii) from about 50% to about 70% gum arabic In a yet another non-limiting example of this embodiment, the composition comprises:
- i) from about 1% to about 15% by weight of an active base, comprising:
  - a) from about 25% to about 50% by weight of ebastine;
  - b) from about 50% to about 75% by weight of sunflower oil; and
- ii) from about 50% to about 70% gum arabic.

Another iteration of this aspect relates to compositions comprising:
- a) one or more protease inhibitors chosen from amprenavir (or the pro-drug fosamprenavir), atazanavir, boceprevir, darunavir, indinavir, lopinavir, nelfinavir, ritonavir, saquinavir, simeprevir, telaprevir, or tipranavir;
- b) a bioavailability enhancing agent chosen from palm kernel oil, soybean oil, rapeseed oil (canola), sunflower oil, groundnut oil, sesame oil, flaxseed oil, palm oil, olive oil and corn oil;
- c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof; and
- d) one or more bile salts.

One embodiment of this iteration relates to compositions comprising:
- a) one or more protease inhibitors chosen from amprenavir (or the pro-drug fosamprenavir), atazanavir, boceprevir, darunavir, indinavir, lopinavir, nelfinavir, ritonavir, saquinavir, simeprevir, telaprevir, or tipranavir;
- b) a bioavailability enhancing agent is sunflower oil;
- c) one or more emulsifiers chosen from gum arabic, propylene glycol, or mixtures thereof; and
- d) ox bile.

One non-limiting example of this embodiment is a composition comprising:
- a) from about 3% to about 6% by weight of darunavir;
- b) from about 5% to about 15% by weight of sunflower oil;
- c) an emulsifier system containing:
  - i) from about 60% to about 70% by weight of the composition gum arabic; and
  - ii) from about 3% to about 10% by weight of the composition propylene glycol; and
- d) from about 5% to about 12% by weight ox bile.

This example can further comprise one or more anti-caking agents. For example, a composition containing silicon dioxide as an anti-caking agent, comprising:
- a) 4.4% darunavir;
- b) 8.9% sunflower oil;
- c) 63.3% gum arabic;
- d) 9% ox bile;
- e) 10% silicon dioxide; and
- f) 4.4% propylene glycol.

Another non-limiting example of this embodiment is a composition comprising:
a) from about 3% to about 6% by weight of bepredil;
b) from about 5% to about 15% by weight of sunflower oil;
c) an emulsifier system containing:
  i) from about 60% to about 70% by weight of the composition gum arabic; and
  ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% bepredil;
b) 8.9% sunflower oil;
c) 63.3% gum arabic;
d) 9% ox bile;
e) 10% silicon dioxide; and
f) 4.4% propylene glycol A further non-limiting example of this embodiment is a composition comprising:
a) from about 3% to about 6% by weight of rupintrivir;
b) from about 5% to about 15% by weight of sunflower oil;
c) an emulsifier system containing:
  i) from about 60% to about 70% by weight of the composition gum arabic; and
  ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% rupintrivir;
b) 8.9% sunflower oil;
c) 63.3% gum arabic;
d) 9% ox bile;
e) 10% silicon dioxide; and
f) 4.4% propylene glycol.

A still further non-limiting example of this embodiment is a composition comprising:
a) from about 3% to about 6% by weight of ebastine;
b) from about 5% to about 15% by weight of sunflower oil;
c) an emulsifier system containing:
  i) from about 60% to about 70% by weight of the composition gum arabic; and
  ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% ebastine;
b) 8.9% sunflower oil;
c) 63.3% gum arabic;
d) 9% ox bile;
e) 10% silicon dioxide; and
f) 4.4% propylene glycol.

In another iteration of this aspect, the compositions comprises:
a) an effective amount of one or more nucleoside reverse transcriptase inhibitors chosen from doravirine, efavirenz, etravirine, loviride, or rilpivirine;
b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof.

In one embodiment of this iteration, the composition comprises:
a) an effective amount of one or more nucleoside reverse transcriptase inhibitors chosen from doravirine, efavirenz, etravirine, loviride, or rilpivirine;
b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
c) gum arabic.

In one non-limiting example of this embodiment, the composition comprises:
i) from about 5% to about 20% by weight of an active base, comprising:
  a) from about 25% to about 50% by weight of efavirenz;
  b) from about 50% to about 75% by weight of sunflower oil; and
ii) from about 50% to about 70% gum arabic;
iii) the balance carriers and other adjunct ingredients.

In another non-limiting example of this embodiment, the composition comprises:
i) from about 1% to about 15% by weight of an active base, comprising:
  a) from about 25% to about 50% by weight of doravirine;
  b) from about 50% to about 75% by weight of sunflower oil; and
ii) from about 50% to about 70% gum arabic.

In a further non-limiting example of this embodiment, the composition comprises:
i) from about 1% to about 15% by weight of an active base, comprising:
  a) from about 25% to about 50% by weight of etravirine;
  b) from about 50% to about 75% by weight of sunflower oil; and ii) from about 50% to about 70% gum arabic In a yet another non-limiting example of this embodiment, the composition comprises:
  i) from about 1% to about 15% by weight of an active base, comprising:
    a) from about 25% to about 50% by weight of loviride;
    b) from about 50% to about 75% by weight of sunflower oil; and
  ii) from about 50% to about 70% gum arabic.

In still further non-limiting example of this embodiment, the composition comprises:
  i) from about 1% to about 15% by weight of an active base, comprising:
    a) from about 25% to about 50% by weight of rilpivirine;
    b) from about 50% to about 75% by weight of sunflower oil; and
  ii) from about 50% to about 70% gum arabic Another further iteration of this aspect relates to compositions comprising:
  a) one or more one or more nucleoside reverse transcriptase inhibitors chosen from doravirine, efavirenz, etravirine, loviride, or rilpivirine;
  b) a bioavailability enhancing agent chosen from palm kernel oil, soybean oil, rapeseed oil (canola), sunflower oil, groundnut oil, sesame oil, flaxseed oil, palm oil, olive oil and corn oil;
  c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof; and
  d) one or more bile salts.

One embodiment of this iteration relates to compositions comprising:
  a) one or more one or more nucleoside reverse transcriptase inhibitors chosen from doravirine, efavirenz, etravirine, loviride, or rilpivirine;
  b) a bioavailability enhancing agent is sunflower oil;
  c) one or more emulsifiers chosen from gum arabic, propylene glycol, or mixtures thereof; and
  d) ox bile.

One non-limiting example of this embodiment is a composition comprising:
  a) from about 3% to about 6% by weight of doravirine;
  b) from about 5% to about 15% by weight of sunflower oil;
  c) an emulsifier system containing:
    i) from about 60% to about 70% by weight of the composition gum arabic; and
    ii) from about 3% to about 10% by weight of the composition propylene glycol; and
  d) from about 5% to about 12% by weight ox bile.

This example can further comprise one or more anti-caking agents. For example, a composition containing silicon dioxide as an anti-caking agent, comprising:
  a) 4.4% doravirine;
  b) 8.9% sunflower oil;
  c) 63.3% gum arabic;
  d) 9% ox bile;
  e) 10% silicon dioxide; and
  f) 4.4% propylene glycol.

One non-limiting example of this embodiment is a composition comprising:
  a) from about 3% to about 6% by weight of efavirenz;
  b) from about 5% to about 15% by weight of sunflower oil;
  c) an emulsifier system containing:
    i) from about 60% to about 70% by weight of the composition gum arabic; and
    ii) from about 3% to about 10% by weight of the composition propylene glycol; and
  d) from about 5% to about 12% by weight ox bile.

This example can further comprise one or more anti-caking agents. For example, a composition containing silicon dioxide as an anti-caking agent, comprising:
  a) 4.4% efavirenz;
  b) 8.9% sunflower oil;
  c) 63.3% gum arabic;
  d) 9% ox bile;
  e) 10% silicon dioxide; and
  f) 4.4% propylene glycol In another non-limiting example of this embodiment is a composition comprising:
  a) from about 3% to about 6% by weight of etravirine;
  b) from about 5% to about 15% by weight of sunflower oil;
  c) an emulsifier system containing:
    i) from about 60% to about 70% by weight of the composition gum arabic; and
    ii) from about 3% to about 10% by weight of the composition propylene glycol; and
  d) from about 5% to about 12% by weight ox bile.

This example can further comprise one or more anti-caking agents. For example, a composition containing silicon dioxide as an anti-caking agent, comprising:
  a) 4.4% etravirine;
  b) 8.9% sunflower oil;
  c) 63.3% gum arabic;
  d) 9% ox bile;
  e) 10% silicon dioxide; and
  f) 4.4% propylene glycol.

In as still further non-limiting example of this embodiment is a composition comprising:
  a) from about 3% to about 6% by weight of loviride;
  b) from about 5% to about 15% by weight of sunflower oil;
  c) an emulsifier system containing:
    i) from about 60% to about 70% by weight of the composition gum arabic; and
    ii) from about 3% to about 10% by weight of the composition propylene glycol; and
  d) from about 5% to about 12% by weight ox bile.

This example can further comprise one or more anti-caking agents. For example, a composition containing silicon dioxide as an anti-caking agent, comprising:
a) 4.4% loviride;
b) 8.9% sunflower oil;
c) 63.3% gum arabic;
d) 9% ox bile;
e) 10% silicon dioxide; and
f) 4.4% propylene glycol.

A yet still further non-limiting example of this embodiment is a composition comprising:
a) from about 3% to about 6% by weight of rilpivirine;
b) from about 5% to about 15% by weight of sunflower oil;
c) an emulsifier system containing:
  i) from about 60% to about 70% by weight of the composition gum arabic; and
  ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% rilpivirine;
b) 8.9% sunflower oil;
c) 63.3% gum arabic;
d) 9% ox bile;
e) 10% silicon dioxide; and
f) 4.4% propylene glycol.

In a yet further iteration of this aspect, the compositions comprises:
a) an effective amount of one or more active agents;
b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof.

In one embodiment of this iteration, the composition comprises:
a) an effective amount of one or more antivirals chosen from GS-441524, remdesivir, indinavir, raltegravir, nevirapine, or azidothymidine;
b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof.

In another embodiment of this iteration, the composition comprises:
a) an effective amount of one or more antivirals chosen from GS-441524, remdesivir, indinavir, raltegravir, nevirapine, or azidothymidine;
b) an effective amount of an edible oil bioavailability enhancing agent chosen from palm kernel oil, soybean oil, rapeseed oil (canola), sunflower oil, groundnut oil, sesame oil, flaxseed oil, palm oil, olive oil or corn oil; and
c) gum arabic.

In one non-limiting example of this embodiment, the composition comprises:
i) from about 5% to about 20% by weight of an active base, comprising:
  a) from about 25% to about 50% by weight of GS-441524;
  b) from about 50% to about 75% by weight of sunflower oil; and
ii) from about 50% to about 70% gum arabic;
iii) the balance carriers and other adjunct ingredients.

In another non-limiting example of this embodiment, the composition comprises:
i) from about 1% to about 15% by weight of an active base, comprising:
  a) from about 25% to about 50% by weight of remdesivir;
  b) from about 50% to about 75% by weight of sunflower oil; and
ii) from about 50% to about 70% gum arabic.

In a further non-limiting example of this embodiment, the composition comprises:
i) from about 1% to about 15% by weight of an active base, comprising:
  a) from about 25% to about 50% by weight of indinavir;
  b) from about 50% to about 75% by weight of sunflower oil; and ii) from about 50% to about 70% gum arabic In another non-limiting example of this embodiment, the composition comprises:
  i) from about 1% to about 15% by weight of an active base, comprising:
    a) from about 25% to about 50% by weight of raltegravir;
    b) from about 50% to about 75% by weight of sunflower oil; and
  ii) from about 50% to about 70% gum arabic.

In a yet another non-limiting example of this embodiment, the composition comprises:
  i) from about 1% to about 15% by weight of an active base, comprising:
    a) from about 25% to about 50% by weight of nevirapine;
    b) from about 50% to about 75% by weight of sunflower oil; and
  ii) from about 50% to about 70% gum arabic.

In a still further non-limiting example of this embodiment, the composition comprises:
  i) from about 1% to about 15% by weight of an active base, comprising:
    a) from about 25% to about 50% by weight of azidothymidine;
    b) from about 50% to about 75% by weight of sunflower oil; and
  ii) from about 50% to about 70% gum arabic.

In a still yet further non-limiting example of this embodiment, the composition comprises:
  i) from about 5% to about 20% by weight of an active base, comprising:
    a) from about 25% to about 50% by weight of colchicine;
    b) from about 50% to about 75% by weight of sunflower oil; and
  ii) from about 50% to about 70% gum arabic;
  iii) the balance carriers and other adjunct ingredients.

A still yet further iteration of this aspect relates to compositions comprising:
  a) an effective amount of one or more antivirals chosen from GS-441524, remdesivir, indinavir, raltegravir, nevirapine, or azidothymidine;
  b) a bioavailability enhancing agent chosen from palm kernel oil, soybean oil, rapeseed oil (canola), sunflower oil, groundnut oil, sesame oil, flaxseed oil, palm oil, olive oil and corn oil;
  c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof; and
  d) one or more bile salts.

One embodiment of this iteration relates to compositions comprising:
  a) an effective amount of one or more antivirals chosen from GS-441524, remdesivir, indinavir, raltegravir, nevirapine, or azidothymidine;
  b) a bioavailability enhancing agent is sunflower oil;
  c) an emulsifier chosen from gum arabic, propylene glycol, or mixtures thereof; and
  d) ox bile.

One non-limiting example of this embodiment is a composition comprising:
  a) from about 3% to about 6% by weight of GS-441524;
  b) from about 5% to about 15% by weight of sunflower oil;
  c) an emulsifier system containing:
    i) from about 60% to about 70% by weight of the composition gum arabic; and
    ii) from about 3% to about 10% by weight of the composition propylene glycol; and
  d) from about 5% to about 12% by weight ox bile.

This example can further comprise one or more anti-caking agents. For example, a composition containing silicon dioxide as an anti-caking agent, comprising:
  a) 4.4% GS-441524;
  b) 8.9% sunflower oil;
  c) 63.3% gum arabic;
  d) 9% ox bile;
  e) 10% silicon dioxide; and
  f) 4.4% propylene glycol.

Another non-limiting example of this embodiment is a composition comprising:
  a) from about 3% to about 6% by weight of remdesivir;
  b) from about 5% to about 15% by weight of sunflower oil;
  c) an emulsifier system containing:
    i) from about 60% to about 70% by weight of the composition gum arabic; and
    ii) from about 3% to about 10% by weight of the composition propylene glycol; and
  d) from about 5% to about 12% by weight ox bile.

This example can further comprise one or more anti-caking agents. For example, a composition containing silicon dioxide as an anti-caking agent, comprising:
  a) 4.4% remdesivir;
  b) 8.9% sunflower oil;
  c) 63.3% gum arabic;
  d) 9% ox bile;
  e) 10% silicon dioxide; and
  f) 4.4% propylene glycol A further non-limiting example of this embodiment is a composition comprising:
  a) from about 3% to about 6% by weight of indinavir;
  b) from about 5% to about 15% by weight of sunflower oil;
  c) an emulsifier system containing:
    i) from about 60% to about 70% by weight of the composition gum arabic; and
    ii) from about 3% to about 10% by weight of the composition propylene glycol; and
  d) from about 5% to about 12% by weight ox bile.

This example can further comprise one or more anti-caking agents. For example, a composition containing silicon dioxide as an anti-caking agent, comprising:
a) 4.4% indinavir;
b) 8.9% sunflower oil;
c) 63.3% gum arabic;
d) 9% ox bile;
e) 10% silicon dioxide; and
f) 4.4% propylene glycol.

A yet further non-limiting example of this embodiment is a composition comprising:
a) from about 3% to about 6% by weight of raltegravir;
b) from about 5% to about 15% by weight of sunflower oil;
c) an emulsifier system containing:
   i) from about 60% to about 70% by weight of the composition gum arabic; and
   ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% raltegravir;
b) 8.9% sunflower oil;
c) 63.3% gum arabic;
d) 9% ox bile;
e) 10% silicon dioxide; and
f) 4.4% propylene glycol.

A yet another non-limiting example of this embodiment is a composition comprising:
a) from about 3% to about 6% by weight of nevirapine;
b) from about 5% to about 15% by weight of sunflower oil;
c) an emulsifier system containing:
   i) from about 60% to about 70% by weight of the composition gum arabic; and
   ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% nevirapine;
b) 8.9% sunflower oil;
c) 63.3% gum arabic;
d) 9% ox bile;
e) 10% silicon dioxide; and
f) 4.4% propylene glycol.

A still yet further non-limiting example of this embodiment is a composition comprising:
a) from about 3% to about 6% by weight of azidothymidine;
b) from about 5% to about 15% by weight of sunflower oil;
c) an emulsifier system containing:
   i) from about 60% to about 70% by weight of the composition gum arabic; and
   ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% azidothymidine;
b) 8.9% sunflower oil;
c) 63.3% gum arabic;
d) 9% ox bile;
e) 10% silicon dioxide; and
f) 4.4% propylene glycol.

All of the above disclosed aspects, iterations, embodiments and examples can further comprise one or more of the disclosed adjunct ingredients.

Another still yet further iteration of this aspect relates to compositions comprising:
a) an effective amount of colchicine;
b) a bioavailability enhancing agent chosen from palm kernel oil, soybean oil, rapeseed oil (canola), sunflower oil, groundnut oil, sesame oil, flaxseed oil, palm oil, olive oil and corn oil;
c) one or more emulsifiers chosen from gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, or mixtures thereof; and
d) one or more bile salts.

One embodiment of this iteration relates to compositions comprising:
a) an effective amount of colchicine;
b) a bioavailability enhancing agent is sunflower oil;
c) an emulsifier chosen from gum arabic, propylene glycol, or mixtures thereof; and
d) ox bile.

One non-limiting example of this embodiment is a composition comprising:
a) from about 3% to about 6% by weight of colchicine;
b) from about 5% to about 15% by weight of sunflower oil;
c) an emulsifier system containing:
   i) from about 60% to about 70% by weight of the composition gum arabic; and
   ii) from about 3% to about 10% by weight of the composition propylene glycol; and
d) from about 5% to about 12% by weight ox bile.

This example can further comprise one or more anti-caking agents. For example, a composition containing silicon dioxide as an anti-caking agent, comprising:
a) 4.4% colchicine;
b) 8.9% sunflower oil;
c) 63.3% gum arabic;
d) 9% ox bile;
e) 10% silicon dioxide; and
f) 4.4% propylene glycol.

All of the above disclosed aspects, iterations, embodiments and examples can further comprise one or more of the disclosed adjunct ingredients.

Methods

Disclosed herein are methods for treating a subject having a viral infection. The methods comprise administering to a person infected with a virus an effective amount of a composition comprising:
  a) one or more antiviral agents; and
  b) a bioavailability enhancing agent.

The disclosed methods can also comprise administering to a person infected with a virus an effective amount of a composition comprising:
  a) one or more anti-inflammatories; and
  b) a bioavailability enhancing agent.

The disclosed methods can further comprise administering to a person infected with a virus an effective amount of a composition comprising:
  a) one or more antiviral agents and an anti-inflammatory agent; and
  b) a bioavailability enhancing agent.

In a further aspect of the presently disclosed methods comprises administering to a subject infected with a virus and effective amount of a composition comprising:
  a) one or more antiviral agents;
  b) a bioavailability enhancing agent; and
  c) an emulsifier.

In a still further aspect of the presently disclosed methods comprises administering to a subject infected with a virus and effective amount of a composition comprising:
  a) one or more antiviral agents;
  b) a bioavailability enhancing agent;
  c) an emulsifier; and
  d) one or more adjunct ingredients.

The methods include the use of any of the disclosed compositions. The methods of use relate to oral dosing of the compositions. The compositions will include, as noted above, an effective amount of a virus inhibitor in combination with a pharmaceutically acceptable carrier and, in addition, can include other medicinal agents, pharmaceutical agents, carriers, adjuvants, diluents, etc. as adjunct ingredients described herein above preferably in unit dosage form suitable for single administration of a precise dosage.

EXAMPLES

Disclosed herein are the following non-limiting examples of the disclosed compositions.

General Process

One or more antiviral agents are combined with a bioavailability enhancing agent and the ingredients are heated and thoroughly admixed to render a homogenous composition wherein the triglycerides and the antiviral agents are in intimate contact. A comestible agent is added and the ingredients further admixed. The composition is then subjected to dehydration, lyophilization or other drying methods to remove all water and volatiles resulting in free flowing powder. The composition is then combined with one or more adjunct ingredients. The final powder can be further processed to produce the desired particle size range. The final powder can also be further combined with one or more emulsifiers and/or surfactants in an aqueous preparation together with processing via high pressure homogenization or ultrasonication to render a liquid nanoemulsified format with a desired particle size range. The final powder and/or liquid nanoemulsion can also be further combined with one or more ingredients used to formulate topical creams, lotions, ointments, gels, balms or other topical dosage forms to render a preparation suitable for application to the peripheral epidermal and/or mucosal membranes.

As disclosed herein above, the disclosed compositions can comprise an emulsifier system or solubilizing system comprising an emulsifier and a solubilizing carrier. For example:

i) an emulsifier; and ii) a carrier.

Typically, after addition of the active base and emulsifier, one or more components may remain not fully dissolved. In that case the formulator can add a carrier to achieve composition homogeneity.

For example:

i) from about 85% to about 95% an emulsifier; and ii) from about 5% to about 15 a carrier.

The formulator can combine the active base with the components the solubilizing system in any order. For example, combining an antiviral with an edible oil followed by a carrier to form a homogeneous admixture prior to addition of the emulsifier.

Non limiting examples of compositions can be found in the following Tables:

TABLE I

| | milligrams | | | | |
|---|---|---|---|---|---|
| | 1 | 2 | 3 | 4 | 5 |
| efavirenz | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE II

| | milligrams | | | | |
|---|---|---|---|---|---|
| | 6 | 7 | 8 | 9 | 10 |
| efavirenz | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE III

| | milligrams | | | | |
|---|---|---|---|---|---|
| | 11 | 12 | 13 | 14 | 15 |
| darunavir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE IV

| | milligrams | | | | |
|---|---|---|---|---|---|
| | 16 | 17 | 18 | 19 | 20 |
| darunavir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE V

| | milligrams | | | | |
|---|---|---|---|---|---|
| | 21 | 22 | 23 | 24 | 25 |
| bepredil | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE VI

| | milligrams | | | | |
|---|---|---|---|---|---|
| | 26 | 27 | 28 | 29 | 30 |
| bepridil | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE VII

| | milligrams | | | | |
|---|---|---|---|---|---|
| | 31 | 32 | 33 | 34 | 35 |
| rupintrivir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE VIII

| | milligrams | | | | |
|---|---|---|---|---|---|
| | 36 | 37 | 38 | 39 | 40 |
| rupintrivir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE IX

| | milligrams | | | | |
|---|---|---|---|---|---|
| | 41 | 42 | 43 | 44 | 45 |
| ebastine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE X

| | milligrams | | | | |
|---|---|---|---|---|---|
| | 46 | 47 | 48 | 49 | 50 |
| ebastine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XI

| | milligrams | | | | |
|---|---|---|---|---|---|
| | 51 | 52 | 53 | 54 | 55 |
| doravirine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE XII

| | milligrams | | | | |
|---|---|---|---|---|---|
| | 56 | 57 | 58 | 59 | 60 |
| doravirine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XIII

| | milligrams | | | | |
|---|---|---|---|---|---|
| | 61 | 62 | 63 | 64 | 65 |
| etravirine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE XIV

| | milligrams | | | | |
|---|---|---|---|---|---|
| | 66 | 67 | 68 | 69 | 70 |
| etravirine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |

TABLE XIV-continued

| | milligrams | | | | |
|---|---|---|---|---|---|
| | 66 | 67 | 68 | 69 | 70 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XV

| | milligrams | | | | |
|---|---|---|---|---|---|
| | 71 | 72 | 73 | 74 | 75 |
| loviride | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE XVI

| | milligrams | | | | |
|---|---|---|---|---|---|
| | 76 | 77 | 78 | 79 | 80 |
| loviride | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XVII

| | milligrams | | | | |
|---|---|---|---|---|---|
| | 81 | 82 | 83 | 84 | 85 |
| rilpivirine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE XVIII

| | milligrams | | | | |
|---|---|---|---|---|---|
| | 86 | 87 | 88 | 89 | 90 |
| rilprivirine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XIX

| | milligrams | | | | |
|---|---|---|---|---|---|
| | 91 | 92 | 93 | 94 | 95 |
| GS-441524 | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |

TABLE XIX-continued

| | milligrams | | | | |
|---|---|---|---|---|---|
| | 91 | 92 | 93 | 94 | 95 |
| ox bile | 90 | 72 | 58.5 | 51.3 | 65.7 |
| propylene glycol | 44 | 35.2 | 28.6 | 25.1 | 32.1 |

TABLE XX

| | milligrams | | | | |
|---|---|---|---|---|---|
| | 96 | 97 | 98 | 99 | 100 |
| GS-441524 | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XXI

| | milligrams | | | | |
|---|---|---|---|---|---|
| | 101 | 102 | 103 | 104 | 105 |
| remdesivir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE XXII

| | milligrams | | | | |
|---|---|---|---|---|---|
| | 106 | 107 | 108 | 109 | 110 |
| remdesivir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XXIII

| | milligrams | | | | |
|---|---|---|---|---|---|
| | 111 | 112 | 113 | 114 | 115 |
| indinavir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE XXIV

| | milligrams | | | | |
|---|---|---|---|---|---|
| | 116 | 117 | 118 | 119 | 120 |
| indinavir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |

TABLE XXIV-continued

| | milligrams | | | | |
|---|---|---|---|---|---|
| | 116 | 117 | 118 | 119 | 120 |
| propylene glycol | 44 | 35.2 | 28.6 | 25.1 | 32.1 |
| silicon dioxide | 100 | 80 | 65 | 57 | 73 |

TABLE XXV

| | milligrams | | | | |
|---|---|---|---|---|---|
| | 121 | 122 | 123 | 124 | 125 |
| raltegravir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |

TABLE XXVI

| | milligrams | | | | |
|---|---|---|---|---|---|
| | 126 | 127 | 128 | 129 | 130 |
| raltegravir | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| silicon dioxide | 100 | 80 | 65 | 57 | 73 |

TABLE XXVII

| | milligrams | | | | |
|---|---|---|---|---|---|
| | 131 | 132 | 133 | 134 | 135 |
| colchicine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| ethanol | 44 | 35.2 | 28.6 | 25.1 | 32.1 |

TABLE XXVIII

| | milligrams | | | | |
|---|---|---|---|---|---|
| | 136 | 137 | 138 | 139 | 140 |
| colchicine | 44 | 35.2 | 28.6 | 25.1 | 32.1 |
| sunflower oil | 89 | 71.2 | 57.9 | 50.7 | 65 |
| gum arabic | 633 | 506.4 | 411.5 | 360.8 | 462.1 |
| ox bile | 90 | 72 | 58.5 | 51.3 | 65.7 |
| propylene glycol | 44 | 35.2 | 28.6 | 25.1 | 32.1 |
| ethanol | 100 | 80 | 65 | 57 | 73 |

The disclosed oral solid compositions can be prepared by conventional methods of blending, filling or tableting. The blending operation can be repeated to distribute the active principle throughout compositions containing large quantities of adjunct ingredients. Such operations are conventional. Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatine, hydroxyethyl cellulose, carboxymethyl cellulose, aluminium stearate gel, or hydrogenated edible fats; emulsifying agents, such as lecithin, sorbitan monooleate, or acacia; non-aqueous vehicles oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

The compounds and compositions, according to the disclosed methods can be administered using any amount. The exact amount required will vary from subject to subject, depending on the age, and general condition of the subject, the severity of the viral infection, the particular antiviral agent. Compounds of the invention are preferably formulated in dosage unit form for ease of administration and uniformity of dosage. The expression "dosage unit form" as used herein refers to a physically discrete unit of an agent appropriate for the patient to be treated. It will be understood, however, that the total daily usage of the compounds and compositions disclosed herein will be decided by the attending physician within the scope of sound medical judgment. The specific effective dose level for any particular patient will depend upon a variety of factors including the disorder being treated and the severity of the disorder; the activity of the specific compound employed; the specific composition employed; the age, body weight, general health, sex and diet of the patient; the time of administration, and rate of excretion of the specific antiviral agent employed; the duration of the treatment; drugs used in combination or coincidental with the specific compound employed, and like factors well known in the medical arts.

Liquid Formulations

A composition comprising the active base is added to a "sugar syrup." The sugar syrup is prepared by dissolving in aqueous solution appropriate quantities of sugar, citric acid, preservatives, glycerin to obtain clear homogenous syrup. The filtered solution of extracts is added to syrup and stirred to obtain a homogenous syrup. The sugars are any pharmaceutically acceptable sugars, for example, monosaccharides include fructose, galactose glucose and dextrose. Disaccharides include lactose, maltose and sucrose. The disclosed syrups can also comprise sugar alcohols, for example, erythritol, glycerol, mannitol, sorbitol, or xylitol. One or more polysaccharides can also be added to adjust the viscosity of the resulting liquid formulation.

Colors, menthol and other flavoring agents along with other commonly known pharmaceutical excipients may be added as required to make this syrup palatable for patients' acceptability.

In general, a liquid formulation can be prepared, for example, by combining a dehydrated free-flowing solid composition comprising:
  i) from about 5% to about 20% by weight of an active base, comprising:
    a) from about 25% to about 50% by weight of darunavir;
    b) from about 50% to about 75% by weight of sunflower oil; and
  ii) from about 50% to about 70% gum arabic;
and a sugar syrup, mixing the admixture until the solution is homogeneous. The formulator can adjust the amount of the active base in order to deliver a desired unit dose of the anti-viral agents, for example, from about 100 mg/dose to about 300 mg/dose.

A non-limiting example of a single dose liquid formulation comprises:
a) 20% darunavir;
b) 40% sunflower oil;
c) 10% gum arabic; and
d) the balance sugar syrup.

Disclosed herein are nanoemulsions of the antiviral compositions disclosed herein above. Once the formulator has selected the active base to be delivered into a liquid formulation the nanoemulsion is then prepared. The nanoemulsion is obtained according to the procedures disclosed herein. The disclosed nanoemulsions are thermodynamically stable, for example high kinetic stability, with low viscosity and optical transparency.

The term "saponin" refers to compounds derived from various plant species, particularly amphipathic glycosides having emulsifier or surfactant properties.

Saponins

The process for preparing the disclosed nanoemulsions uses emulsifiers and surfactants to obtain the desired properties. In one aspect the disclosed process utilizes saponins for their emulsification properties.

The disclosed saponins are obtained from naturally occurring sources, for example, the genus *Saponaria*, of the family Caryophyllaceae; *Sapindus* of the family Sapindaceae; in the families Sapindaceae, Hippocastanaceae, *Gynostemma* (*G. pentaphyllum* sp.), and Cucurbitaceae. In addition, saponins can be derived from the genus *Panax*, for example, *Panax quinquefolius, Panax vietnamensis,* and *Panax pseudoginseng*. One non-limiting example of a suitable saponin is "soap bark" obtained from *Quillaja saponaria*, herein referred to as "quillaja."

In one aspect the disclosed nanoemulsions have an average droplet size from about 50 nm to about 1,000 nm. In one embodiment the droplet size is from about 10 nm to about 500 nm. In a further embodiment the droplet size is from about 100 to about 500 nm. In a yet further embodiment the droplet size is from about 200 to about 800 nm. In a still further embodiment the droplet size is from about 400 to about 800 nm.

Disclosed herein is a nanoemulsion, comprising:
A) a first component containing:
  i) from about 5% to about 20% by weight of an active base, comprising:
    a) from about 25% to about 50% by weight of one or more antiviral agents;
    b) from about 50% to about 75% by weight of a bioavailability enhancing agent; and
  ii) from about 50% to about 70% a base substrate; and
B) a second component containing:
  a) an emulsifier; and
  b) water;
wherein the average droplet size is from about 50 nm to about 1,000 nm.

General Process for Preparing the Disclosed Compositions in the Form of a Nanoemulsion One or more biologically active ingredients are combined with a bioavailability enhancing agent and the ingredients are heated and thoroughly admixed to render a homogenous composition wherein the triglycerides and the biologically active ingredients are in intimate contact. A base substrate is added and the ingredients further admixed. The composition is then subjected to dehydration, lyophilization or other drying methods to remove all water and volatiles resulting in free flowing powder. The composition is then combined with one or more optional adjunct ingredients. The final powder can be further processed to produce the desired particle size range.

The control composition comprises:
a) one or more antiviral agents;
b) a bioavailability enhancing agent;
  wherein (a) and (b) are present in a ratio from about 1:1 to about 1:3; and
c) a the base substrate.

General Process for the Formation of Nanoemulsions

Disclosed herein is a general process for preparing a nanoemulsion, comprising:
A) combining one or more antiviral agents and a bioavailability enhancing agent to form an enhanced delivery admixture;
B) combining the enhanced delivery admixture with a base substrate and removing any water present to form a first component;
C) dissolving the first component in aqueous solution of a saponin at a temperature of from about 50° C. to about 60° C. to form an admixture;
D) cooling the admixture in step I to a temperature of from about 40° C. to about 50° C. to form a cooled solution; and
E) high pressure homogenizing the cooled solution at 30,000 psi to form the nanoemulsion.

In one aspect the process for converting the composition to a nanoemulsion, comprises:
3) an aqueous solution of a saponin is heated to a temperature of from about 50° C. to about 60° C. to form an aqueous emulsion;
ii) the fine powder composition is added to the emulsion formed in step (i) and the resulting solution admixed;
iii) the solution of step (ii) is cooled to a temperature of from about 40° C. to about 50° C.; and
iv) the cooled solution was high pressure homogenized at 30,000 psi to form the nanoemulsion.

Example I

A fine powder formulation was prepared according to the General Process. The composition comprised lactose monohydrate powder as a base substrate, high CBD-content multi-spectrum hemp oil available from Alpha *Canna* and high oleic acid sunflower oil in a 1:1 ratio. A surfactant, polysorbate 80 was also added.

Once prepared, the powder formulation was then converted to a nanoemulsion according to the following steps:
3) an aqueous solution of quillaja obtained from *Quillaja saponaria* was heated to a temperature of from about 50° C. to about 60° C. to form an aqueous emulsion;
ii) the fine powder composition was added to the emulsion formed in step (i) and the resulting solution admixed;
iii) the solution of step (ii) is cooled to a temperature of from about 40° C. to about 50° C.; and
iv) the cooled solution was high pressure homogenized at 30,000 psi to form the nanoemulsion.

Example II

A fine powder formulation of the active base containing composition was prepared according to the General Process. The composition comprised lactose monohydrate powder as a base substrate, one or more antiviral agents high oleic acid sunflower oil in a 1:1 ratio. A surfactant, polysorbate 80 was also added.

Once prepared, the powder formulation was then converted to a nanoemulsion according to the following steps:
3) an aqueous solution of quillaja obtained from *Quillaja saponaria* was heated to a temperature of from about 50° C. to about 60° C. to form an aqueous emulsion;
ii) the fine powder composition was added to the emulsion formed in step (i) and the resulting solution admixed;
iii) the solution of step (ii) is cooled to a temperature of from about 40° C. to about 50° C.; and
iv) the cooled solution was high pressure homogenized at 30,000 psi to form the nanoemulsion.

Homogenization

The homogenization step can include microfluidization under high pressure. For example at pressures from about 10,000 psi to about 30,000 psi. In some embodiments a high shear rotostator processor and/or an ultrasonication processor can be used. As known to the formulator these processes vary in efficiency depending on the duration and intensity of the energy applied.

In one embodiment the formulator can apply microfluidization at 30,000 PSI for a "single pass" through the processor or multiple passes through the processor which is more time consuming of course but can lead to better particle size reduction and size distribution homogeneity than a single pass.

Once formed, the nanoemulsion can be dispersed into a sugar syrup. The nanoemulsion-containing sugar syrup can further comprise colorants and/or flavorants.

The disclosed nanoemulsion-containing liquid compositions, comprise:
I) from about 10% to about 15% of a nanoemulsion comprising:
A) a first component containing:
i) from about 5% to about 20% by weight of an active base, comprising:
a) from about 25% to about 50% by weight of one or more antiviral agents;
b) from about 50% to about 75% by weight of a bioavailability enhancing agent; and
ii) from about 50% to about 70% a base substrate; and
  B) a second component containing:
    a) an emulsifier; and
    b) water; and
II) The balance a sugar syrup.

Evaluation of Compositions In Vivo

In this study, the exposure and distribution of darunavir and efavirenz were evaluated following oral administration in male Sprague-Dawley rats. Four cohorts of 10 rats each were used in this study. The first cohort involved darunavir using the disclosed formulations and the second cohort darunavir in a control formulation. The third cohort involved efavirenz using the disclosed formulations and the fourth cohort efavirenz in a control formulation.

Formulations were administered orally (PO) at 10 mg/kg of darunavir or efavirenz. Following dosing, blood, urine and fecal samples were collected up to 8-hour post dose (groups 1, 3, 5, and 7) or 24-hour post dose (groups 2, 4, 6, and 8). Brain tissue was collected at 8 hours or 24 hours, following the 8 hour or 24-hour urine and feces sample collection. Plasma, urine, feces, and brain tissue concentrations of the analytes were determined by LC-MS/MS. Plasma pharmacokinetic parameters were determined using WinNonlin (v8.0) software. A summary of the average plasma exposures and brain tissue concentrations are shown in Table 2 and Table 3, respectively. A summary of the average darunavir or efavirenz recovery in urine and feces are shown in Table 4.

Test Solutions

The following test solutions were prepared for use in the study described herein below 3. Darunavir Test Solution

| Ingredient | percent |
|---|---|
| Darunavir | 4.4 |
| Gum Arabic | 63.3 |
| High oleic sunflower oil | 8.9 |
| Propylene glycol | 4.4 |
| Bile salts | 9 |
| Silicon dioxide | 10 |

The 8-hour dosage test solution (Group #1) was prepared as follows. The above test solution (476.13 mg) is charged to a 23 mL clear glass vial. Water (15 mL) is added to the vial and the solution is vortexed/sonicated, QS to 20.0 mL, resulting in a fine suspension.

The 24-hour dosage test solution (Group #2) was prepared as follows. The above test solution (502.05 mg) is charged to a 23 mL clear glass vial. Water (15 mL) is added to the vial and the solution is vortexed/sonicated, QS to 21.1 mL, resulting in a fine suspension.

2. Darunavir Control Solution

| Ingredient | percent |
|---|---|
| Darunavir | 4.6 |
| Gum Arabic | 85.4 |
| Silicon dioxide | 10 |

The 8-hour dosage control solution (Group #3) was prepared as follows. The above test solution (448.68 mg) is charged to a 23 mL clear glass vial. Water (15 mL) is added to the vial and the solution is vortexed/sonicated, QS to 20.0 mL, resulting in a fine suspension.

The 24-hour dosage control solution (Group #4) was prepared as follows. The above test solution (452.47 mg) is charged to a 23 mL clear glass vial. Water (15 mL) is added to the vial and the solution is vortexed/sonicated, QS to 20.2 mL, resulting in a fine suspension.

3. Efavirenz Test Solution

| Ingredient | percent |
|---|---|
| Efavirenz | 4.4 |
| Gum Arabic | 63.3 |
| High oleic sunflower oil | 8.9 |
| Propylene glycol | 4.4 |
| Bile salts | 9 |
| Silicon dioxide | 10 |

The 8-hour dosage test solution (Group #5) was prepared as follows. The above test solution (482.0 mg) is charged to a 21 mL clear glass vial. Water (15 mL) is added to the vial and the solution is vortexed/sonicated, QS to 20.4 mL, resulting in a fine suspension.

The 24-hour dosage test solution (Group #2) was prepared as follows. The above test solution (481.11 mg) is charged to a 21 mL clear glass vial. Water (15 mL) is added to the vial and the solution is vortexed/sonicated, QS to 20.4 mL, resulting in a fine suspension.

4. Efavirenz Control Solution

| Ingredient | percent |
|---|---|
| Efavirenz | 4.6 |
| Gum Arabic | 85.4 |
| Silicon dioxide | 10 |

The 8-hour dosage control solution (Group #7) was prepared as follows. The above test solution (441.79 mg) is charged to a 21 mL clear glass vial. Water (15 mL) is added to the vial and the solution is vortexed/sonicated, QS to 20.4 mL, resulting in a fine suspension.

The 24-hour dosage control solution (Group #8) was prepared as follows. The above test solution (440.22 mg) is charged to a 21 mL clear glass vial. Water (15 mL) is added to the vial and the solution is vortexed/sonicated, QS to 20.3 mL, resulting in a fine suspension.

Table 1 below discloses the dosing protocol for the present study (No. 1). For example, the 8-hour group #1 and the 24-hour group #2 were dosed with the darunavir test solution.

TABLE 1

| Group # | Test Formulation | Nominal Con. (mg/mL) | Measured Con. (mg/mL) | Measured % of Nominal |
|---|---|---|---|---|
| 1 & 2 | Darunavir Test | 1 | 1.06 ± 0.18 | 106 |
| 3 & 4 | Darunavir Control | 1 | 0.99 ± 0.17 | 99.2 |
| 5 & 6 | Efavirenz Test | 1 | 0.93 ± 0.07 | 92.9 |
| 7 & 8 | Efavirenz Control | 1 | 0.91 ± 0.05 | 91.3 |

Table 2 provides a summary of the average plasma exposures for darunavir and efavirenz after oral administration of the disclosed formulations a 10 mg/kg in male Sprague-Dawley rats.

TABLE 2

| Group # | Test Formulation | $t_{1/2}$ (hr) | Cmax (ng/mL) | tmax (hr) | AUClast (hr · ng/mL) | Dose-normalized AUClast (hr · kg · ng/mL/mg) |
|---|---|---|---|---|---|---|
| 1 & 2 | DAR test | 0.98 ± 0.28 | 509 ± 516 | 0.53 ± 0.28 | 721 ± 332 | 72.1 ± 33.2 |
| 3 & 4 | DAR cont. | 0.72 ± 0.21 | 472 ± 200 | 0.38 ± 0.24 | 469 ± 251 | 46.9 ± 25.1 |
| 5 & 6 | EFA test | 2.75 ± 1.14 | 172 ± 67.9 | 2.00 ± 1.15 | 752 ± 203 | 75.2 ± 20.3 |
| 7 & 8 | EFA cont. | 2.78 ± 1.19 | 153 ± 46.8 | 1.20 ± 0.57 | 650 ± 148 | 65.0 ± 14.8 |

Table 3 is a summary of the average brain tissue concentrations for darunavir and efavirenz after oral administration of the disclosed formulations at 10 mg/kg in male Sprague-Dawley rats.

TABLE 3

| Group # | Test Formulation | Brain Tissue Concentration (ng/g) | |
|---|---|---|---|
| | | 8 hours | 24 hours |
| 1 & 2 | DAR test | ND | ND |
| 3 & 4 | DAR cont. | ND | ND |
| 5 & 6 | EFA test | 166 ± 19.1 | ND |
| 7 & 8 | EFA cont. | 211 ± 56.2 | ND |

ND: not determined because analytical data were BLOQ (below limit of quantification, 10 ng/mL)

Table 4 is a summary of the average urine and feces % if dose recovered for darunavir and efavirenz after oral administration of the disclosed formulations at 10 mg/kg in male Sprague-Dawley rats.

TABLE 4

| Group # | Test Formulation | Urine (%) | | Feces (%) | |
|---|---|---|---|---|---|
| | | 8 hours | 24 hours | 8 hours | 24 hours |
| 1 & 2 | DAR test | 0.0071 ± 0.0028 | 0.0164 ± 0.0118 | 2.00 ± 2.24 | 8.24 ± 1.32 |
| 3 & 4 | DAR cont. | 0.0116 ± 0.0035 | 0.0115 ± 0.0049 | 6.31 ± 4.13 | 10.7 ± 2.33 |
| 5 & 6 | EFA test | ND | ND | 2.27 ± 2.62 | 29.4 ± 7.57 |
| 7 & 8 | EFA cont. | ND | ND | 3.10 ± 2.70 | 31.4 ± 10.0 |

Plasma, urine, feces, and brain tissue samples were extracted and analyzed using the methods described as follows.

Analytical Stock Solution Preparation

Analytical stock solutions (1.00 mg/mL of the free drug) were prepared in DMSO. Sample Homogenization Brain tissue and feces samples were homogenized with a Virsonic 100 ultrasonic homogenizer. Each brain tissue sample was first weighed, and then an appropriate volume of 20:80 methanol:water was added to make a 2 mL/gram sample. Samples were then homogenized on ice, and stored frozen until analysis. Feces samples were homogenized with 20:80 MeOH:water (8 mL/gram of tissue) prior to extraction. Standard Preparation (Plasma, Urine, and Brain) Standards were prepared in rat plasma containing sodium heparin as the anticoagulant, or in blank tissue homogenate. Working solutions were prepared in 50:50 acetonitrile:water. Working solutions were then added to blank matrix to make calibration standards to final concentrations of 1000, 500, 250, 100, 75.0, 50.0, 25.0, and 10 ng/mL. Standards were treated identically to the study samples. Sample Extraction (Plasma, Urine, Feces, and Brain) Plasma, urine, feces, and brain tissue samples were manually extracted via acetonitrile precipitation in a 96-well plate. Urine samples were diluted a minimum of 5-fold into blank rat plasma prior to extraction. Diluted urine samples were quantified against the rat plasma calibration curve. Brain and feces tissue homogenates were quantified against calibration curves prepared in matched blank tissue homogenate.

Table 5 shows the average plasma concentration (ng/mL) of the animals after being given a 10 mg/mL dose of one of the 8 test formulations. The values are the mean plasma level of each group over time.

TABLE 5

| Time (hr) | Mean plasma level in ng/mL | | | |
|---|---|---|---|---|
| | Groups 1 & 2 | Groups 3 & 4 | Groups 5 & 6 | Groups 7 & 8 |
| 0.25 | 444 | 464 | 33.7 | 57.9 |
| 0.5 | 294 | 357 | 76.7 | 102.9 |
| 0.75 | 301 | 236 | 109 | 124 |
| 1 | 306 | 185 | 133 | 139 |
| 2 | 153 | 63.1 | 142 | 117 |
| 4 | 22.6 | 16.6 | 97.7 | 75.9 |
| 8 | 26.6 | * | 54.3 | 44.5 |

* Below the detectable limit

The results of Study No. 1 are summarized in Table 5 and FIG. 1 to FIG. 4. FIG. 1 depicts the average plasma concentration of darunavir in the test solutions. As seen in Table 5 and FIG. 1 the average plasma concentration of darunavir in the test animals at 1 hour is approximately 306 ng/mL and at 2 hours is approximately 153 ng/mL. In contrast, as seen in Table 5 and FIG. 2, the average plasma concentration of darunavir in the animals given the control formulation at 1 hour is approximately 185 ng/mL and at 2 hours is approximately 63 ng/mL. The compositions disclosed herein provide double the plasma concentration of the anti-viral agent darunavir versus compositions that do not comprise the disclosed compositions.

Figure 3:
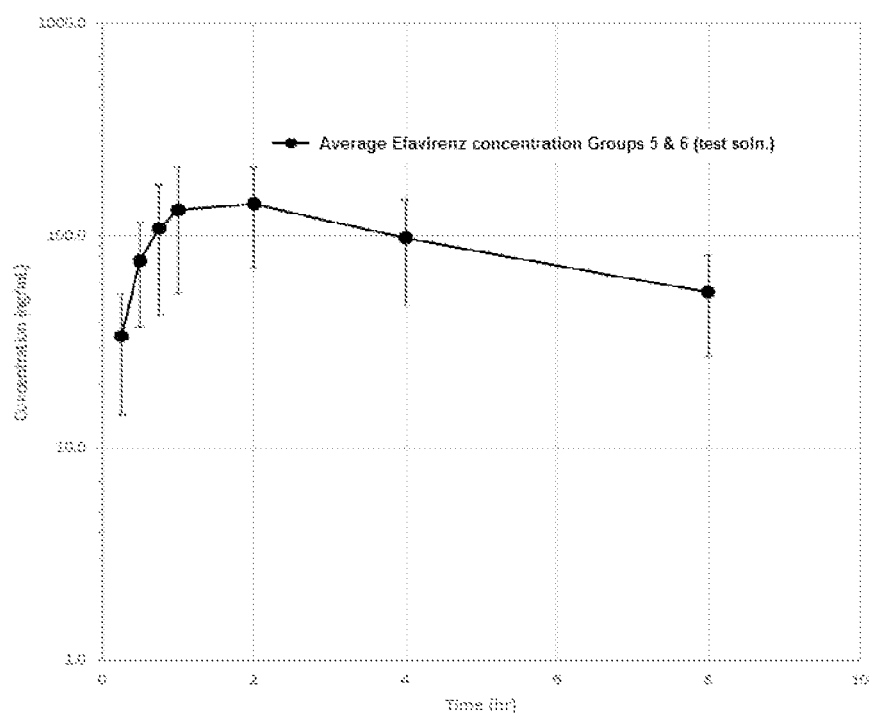
FIG. 3 depicts the average plasma concentration of efavirenz in the test animals at 1 hour is approximately 133 ng/mL and at 2 hours is approximately 142 ng/mL.
Figure 4:
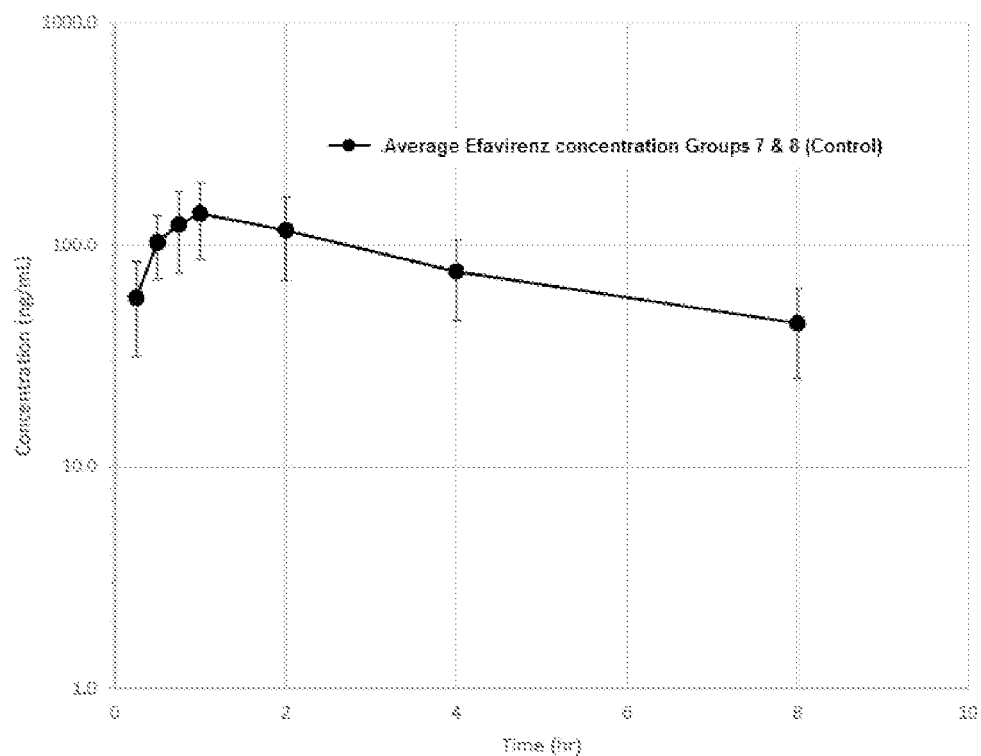
FIG. 4 depicts the average plasma concentration of efavirenz in the animals given the control formulation at 1 hour is approximately 139 ng/mL and at 2 hours is approximately 117 ng/mL.

As seen in Table 5 and FIG. 3 the average plasma concentration of efavirenz in the test animals at 1 hour is approximately 133 ng/mL and at 2 hours is approximately 142 ng/mL. As seen in Table 5 and FIG. 4, the average plasma concentration of efavirenz in the animals given the control formulation at 1 hour is approximately 139 ng/mL and at 2 hours is approximately 117 ng/mL. The formulations disclosed herein provide plasma concentration levels of efavirenz at higher levels than control formulations.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A pharmaceutical composition, comprising:
   a) from about 25 mg to about 300 mg by weight of one or more antiviral agents or a pharmaceutically acceptable salt thereof; and
   b) from about 50 mg to about 600 mg by weight of sunflower oil.

2. The composition according to claim 1, comprising 50 mg to about 150 mg by weight of one or more antiviral agents.

3. The composition according to claim 1, comprising 100 mg to about 200 mg by weight of one or more antiviral agents.

4. The composition according to claim 1, comprising 50 mg to about 100 mg by weight of one or more antiviral agents.

5. The composition according to claim 1, comprising 200 mg to about 300 mg by weight of one or more antiviral agents.

6. The composition according to claim 1, wherein the antiviral agent is selected from the group consisting of protease inhibitors, endonuclease inhibitors, integrase inhibitors, enzyme inhibitors, non-nucleoside reverse transcriptase inhibitors, fusion inhibitors, cell entry inhibitors, mRNA and protein synthesis inhibitors cannabinoids, viral replication blockers, uncoating inhibitors, reverse transcriptase inhibitors, topoisomerase inhibitors, assembly inhibitors, M2 inhibitors, DNA polymerase inhibitors, DNA terminase complex inhibitors, HCV protein inhibitors, neuraminidase inhibitors, and virus-neutralizing antibodies.

7. The composition according to claim 1, wherein the antiviral agent is a protease inhibitor selected from the group consisting of amprenavir, fosamprenavir, atazanavir, bepridil, boceprevir, darunavir, ebastine, indinavir, lopinavir, nelfinavir, ritonavir, rupintrivir, saquinavir, simeprevir, telaprevir, and tipranavir.

8. The composition according to claim 7, wherein the antiviral agent is a Nucleoside Reverse Transcriptase Inhibitors (NNRTI) selected from the group consisting of doravirine, efavirenz, etravirine, loviride, or rilpivirine.

9. The composition according to claim 1, wherein the antiviral agent is selected from the group consisting of cobicistat, baloxavir marboxil, bictegravir, elvitegravir, daclatasvir, maraviroc, umifenovir, methisazone, tromantadine, or rimantadine.

10. The composition according to claim 1, wherein the antiviral agent selected from the group consisting of from (1R,2R,3R,4R,5S)-2-(4-aminopyrrolo[2,1-f][1,2,4]triazin-7-yl)-4,5-dihydroxy-3 (hydroxymethyl)cyclopentanecarbonitrile, remdesivir, sarilumab, indinavir raltegravir, nevirapine, or azidothymidine.

11. The composition according to claim 1, comprising from about 50 mg to about 400 mg of sunflower oil.

12. The composition according to claim 1, comprising from about 100 mg to about 200 mg of sunflower oil.

13. The composition according to claim 1, comprising from about 50 mg to about 400 mg of sunflower oil.

14. The composition according to claim 1, comprising from about 150 mg to about 250 mg of sunflower oil.

15. The composition according to claim 1, comprising from about 200 mg to about 400 mg of sunflower oil.

16. The composition according to claim 1, further comprising a bile acid chosen from cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, or lithocolate wherein the bile acid is conjugated with glycine or taurine to form a salt.

17. The composition according to claim 1, further comprising ox bile.

18. The composition according to claim 1, further comprising a carrier, surfactant, or an anti-caking agent.

19. A pharmaceutical composition, comprising:
a) 4.4% by weight of an antiviral selected from the group consisting of darunavir, bepridil, rupintrivir, ebastine, and mixtures thereof;
b) 8.9% sunflower oil;
c) 63.3% gum arabic;
d) 9% ox bile;
e) 10% silicon dioxide; and
f) 4.4% propylene glycol.

20. A pharmaceutical composition, comprising:
a) 4.4% by weight of an antiviral selected from the group consisting of doravirine, efavirenz, etravirine, loviride, rilpivirine, and mixtures thereof;
b) 8.9% sunflower oil;
c) 63.3% gum arabic;
d) 9% ox bile;
e) 10% silicon dioxide; and
f) 4.4% propylene glycol.

21. A pharmaceutical composition, comprising:
a) 4.4% by weight of an antiviral selected from the group consisting of remdesivir, indinavir, raltegravir, nevirapine, azidothymidine, and mixtures thereof;
b) 8.9% sunflower oil;
c) 63.3% gum arabic;
d) 9% ox bile;
e) 10% silicon dioxide; and
f) 4.4% propylene glycol.

* * * * *